United States Patent
Morimoto et al.

(10) Patent No.: US 9,920,135 B2
(45) Date of Patent: Mar. 20, 2018

(54) ANTI-HUMAN CD26 MONOCLONAL ANTIBODY OR ANTIGEN-BINDING FRAGMENT THEREOF

(71) Applicant: JUNTENDO EDUCATIONAL FOUNDATION, Bunkyo-ku (JP)

(72) Inventors: Chikao Morimoto, Setagaya-ku (JP); Ryo Hatano, Yokohama (JP); Taketo Yamada, Suginami-ku (JP); Kei Ohnuma, Shinagawa-ku (JP)

(73) Assignee: JUNTENDO EDUCATIONAL FOUNDATION, Bunkyo-ku (JP)

( * ) Notice: Subject to any disclaimer, the term of this patent is extended or adjusted under 35 U.S.C. 154(b) by 54 days.

(21) Appl. No.: 14/908,383

(22) PCT Filed: Jul. 30, 2014

(86) PCT No.: PCT/JP2014/070084
§ 371 (c)(1),
(2) Date: Jan. 28, 2016

(87) PCT Pub. No.: WO2015/016267
PCT Pub. Date: Feb. 5, 2015

(65) Prior Publication Data
US 2016/0159925 A1    Jun. 9, 2016

(30) Foreign Application Priority Data

Jul. 31, 2013 (JP) ................................ 2013-158533

(51) Int. Cl.

| | | |
|---|---|---|
| *C07K 16/28* | (2006.01) |
| *C07K 16/30* | (2006.01) |
| *G01N 33/566* | (2006.01) |
| *G01N 33/567* | (2006.01) |
| *C12N 5/18* | (2006.01) |
| *C07K 16/40* | (2006.01) |
| *G01N 33/574* | (2006.01) |
| *G01N 33/577* | (2006.01) |
| *C12N 5/16* | (2006.01) |
| *G01N 33/564* | (2006.01) |
| *G01N 33/569* | (2006.01) |
| *G01N 33/68* | (2006.01) |
| *G01N 33/573* | (2006.01) |
| *A61K 39/00* | (2006.01) |

(52) U.S. Cl.
CPC .......... *C07K 16/40* (2013.01); *C07K 16/2896* (2013.01); *C12N 5/163* (2013.01); *G01N 33/564* (2013.01); *G01N 33/56972* (2013.01); *G01N 33/56983* (2013.01); *G01N 33/573* (2013.01); *G01N 33/574* (2013.01); *G01N 33/577* (2013.01); *G01N 33/57419* (2013.01); *G01N 33/57423* (2013.01); *G01N 33/57434* (2013.01); *G01N 33/6893* (2013.01); *A61K 2039/505* (2013.01); *C07K 2317/24* (2013.01); *C07K 2317/76* (2013.01); *G01N 2333/70596* (2013.01); *G01N 2333/948* (2013.01); *G01N 2500/00* (2013.01); *G01N 2800/042* (2013.01)

(58) Field of Classification Search
CPC .... G01N 33/53; G01N 33/566; G01N 33/573; G01N 33/574; G01N 33/577; G01N 33/58; G01N 33/567; G01N 33/56966; C07K 16/2803; C07K 16/2896; C07K 16/40; C07K 2317/14; C07K 14/0596; C12N 5/10; C12N 5/12; C12N 5/16
See application file for complete search history.

(56) References Cited

U.S. PATENT DOCUMENTS

| | | | |
|---|---|---|---|
| 8,771,688 B2 * | 7/2014 | Morimoto ........ | A61K 31/7088 424/133.1 |
| 2007/0105771 A1 | 5/2007 | Aoyagi et al. | |
| 2009/0136523 A1 | 5/2009 | Aoyagi et al. | |

FOREIGN PATENT DOCUMENTS

| | | |
|---|---|---|
| JP | 2009-502139 A | 1/2009 |
| WO | WO 2007/014169 A2 | 2/2007 |
| WO | 2008/114876 A1 | 9/2008 |

OTHER PUBLICATIONS

Simeoni, L., et al., Human Immunology, 63: 719-730, 2002.*
R.P. Dong, et al., "Correlation of the epitopes defined by anti-CD26 mAbs and CD26 function," Molecular Immunology, vol. 35, 1998, pp. 13-21.
J. Huehn, et al., "The Adenosine Deaminase-Binding Region Is Distinct from Major Anti-CD26 mAb Epitopes on the Human Dipeptidyl Peptidase IV(CD26) Molecule," Cellular Immunology, vol. 192, 1999, pp. 33-40.
C. A. Abbott, et al., "Binding to human dipeptidyl peptidase IV by adenosine deaminase and antibodies that inhibit ligand binding involves overlapping, discontinuous sites on a predicted β propeller domain," European Journal of Biochemistry, vol. 266, 1999, pp. 798-810.

(Continued)

*Primary Examiner* — Misook Yu
*Assistant Examiner* — Anne L Holleran
(74) *Attorney, Agent, or Firm* — Oblon, McClelland, Maier & Neustadt, L.L.P.

(57) ABSTRACT

It is intended to provide an anti-human CD26 antibody which permits analysis, etc., of the expression of CD26 in cancer tissues, immune tissues, or the like, for example, in order to select a patient applicable to treatment or to monitor therapeutic effects, and can also be used in immunostaining. The present invention relates to an anti-human CD26 monoclonal antibody or an antigen-binding fragment thereof, binding to an epitope which is recognized by a monoclonal antibody produced by a hybridoma deposited under Accession No. NITE BP-01642, a hybridoma deposited under Accession No. NITE BP-01643, or a hybridoma deposited under Accession No. NITE BP-01644.

18 Claims, 7 Drawing Sheets

(56) References Cited

OTHER PUBLICATIONS

A. J. Ulmer, et al., "CD26 Antigen is a Surface Dipeptidyl Peptidase IV (DPPIV) as Characterized by Monoclonal Antibodies Clone TII-19-4-7 and 4EL1C7," Scandinavian Journal of Immunology, vol. 31, 1990, pp. 429-435.

D. A. Fox, et al., "$Ta_1$, A Novel 105 KD Human T Cell Activation Antigen Defined by a Monoclonal Antibody," The Journal of Immunology, vol. 133, No. 3, Sep. 1984, pp. 1250-1256.

T. Tanaka, et al., "Cloning and Functional Expression of the T Cell Activation Antigen CD26," The Journal of Immunology, vol. 149, No. 2, Jul. 15, 1992, pp. 481-486.

K. Ohnuma, et al., "Revisiting an old acquaintance: CD26 and its molecular mechanisms in T cell function," Cell Press, 2008, 7 pages.

C. Morimoto, et al., "The structure and function of CD26 in the T-cell immune response," Immunological Reviews, vol. 161, 1998, pp. 55-70.

N. H. Dang, et al., "Cell Surface Modulation of CD26 by Anti-1F7 Monoclonal Antibody Analysis of Surface Expression and Human T Cell Activation," The Journal of Immunology, vol. 145, No. 12, Dec. 15, 1990, pp. 3963-3971.

J. Masuyama, et al., "Characterization of the 4C8 Antigen Involved in Transendothelial Migration of $CD26^{hi}$ T Cells after Tight Adhesion to Human Umbilical Vein Endothelial Cell Monolayers," Journal of Experimental Medicine, vol. 189, No. 6, Mar. 15, 1999, pp. 979-989.

K. Ohnuma, et al., "T-cell activation via CD26 and caveolin-1 in rheumatoid synovium," Modern Rheumatology, vol. 16, 2006, pp. 3-13.

R. Hatano, et al., "CD26-mediated co-stimulation in human $CD8^+$ T cells provokes effector function via pro-inflammatory cytokine production," Immunology: The journal of cells, molecules, systems and technologies, vol. 138, 2012, pp. 165-172.

R. Hatano, et al., "Prevention of acute graft-versus host disease by humanized anti-CD26 monoclonal antibody," British Journal of Hematology, vol. 162, 2013, pp. 263-277.

P. A. Havre, et al., "The role of CD26/dipeptidyl peptidase IV in cancer," Frontiers in Bioscience vol. 13, Jan. 1, 2008, pp. 1634-1645.

U. Yamaguchi, et al., "Distinct Gene Expression-Defined Classes of Gastrointestinal Stromal Tumor," Journal of Clinical Oncology, vol. 26, No. 25, Sep. 1, 2008, pp. 4100-4108.

T. Inamoto, et al., "Humanized Anti-CD26 Monoclonal Antibody as a Treatment for Malignant Mesothelioma Tumors," Clinical Cancer Research, vol. 13, No. 14, Jul. 15, 2007, pp. 4191-4200.

K. Aoe, et al., "CD26 Overexpression Is Associated with Prolonged Survival and Enhanced Chemosensitivity in Malignant Pleural Mesothelioma," Clinical Cancer Research, vol. 18, No. 5, Mar. 1, 2012, p. 1447-1456.

International Search Report dated Oct. 28, 2014 in PCT/JP14/70084 Filed Jul. 30, 2014.

Extended European Search Report dated Dec. 5, 2016 in Patent Application No. 14831681.3.

Ryo Hatano, et al., "Establishment of monoclonal anti-human CD26 antibodies suitable for immunostaining of formalin-fixed tissue" Diagnostic Pathology, vol. 9, No. 1, XP021178896, Feb. 6, 2014, 13 Pages.

Vishwa Jeet Amatya, et al., "Overexpression of CD26/DPPIV in mesothelioma tissue and mesothelioma cell lines" Oncology Reports, vol. 26, XP055322123, Sep. 5, 2011, pp. 1369-1375.

J. J. Van Den Oord, "Expression of CD26/dipeptidyl-peptidase IV in benign and malignant pigment-cell lesions of the skin" British Journal of Dermatology, vol. 138, XP002944502, Apr. 1, 1998, pp. 615-621.

\* cited by examiner

[Figure 1]
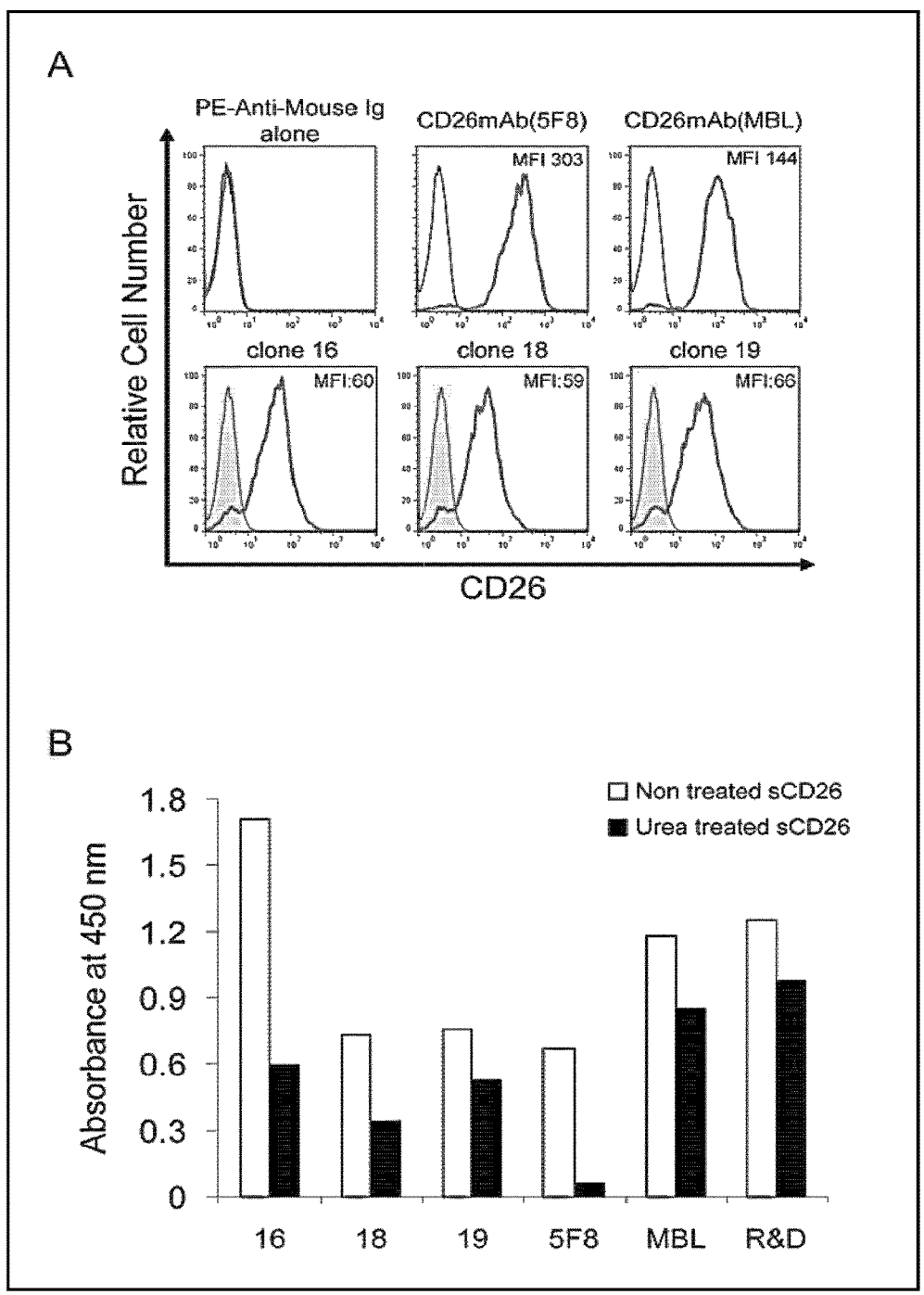

[Figure 2A]
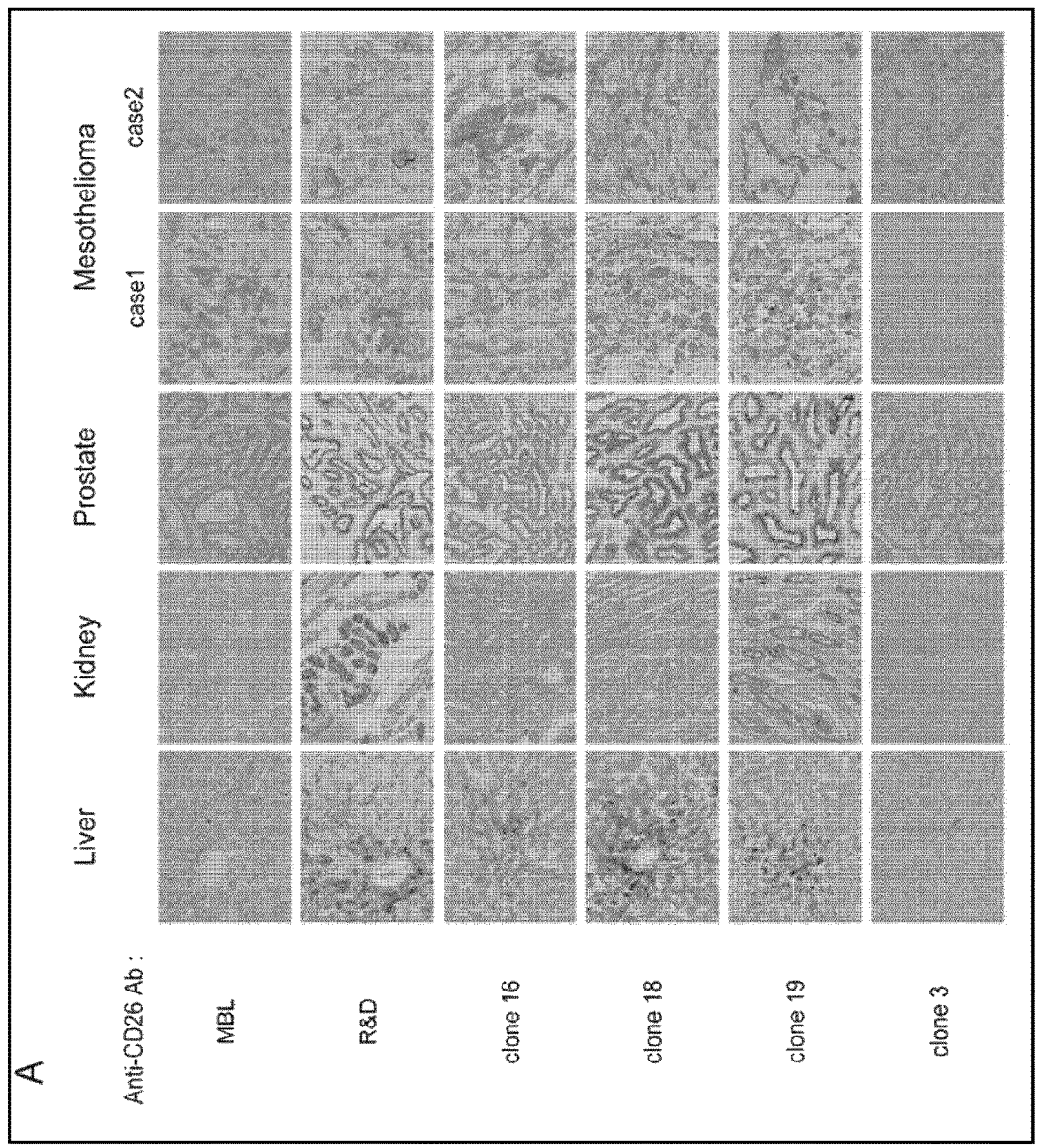

[Figure 2B]
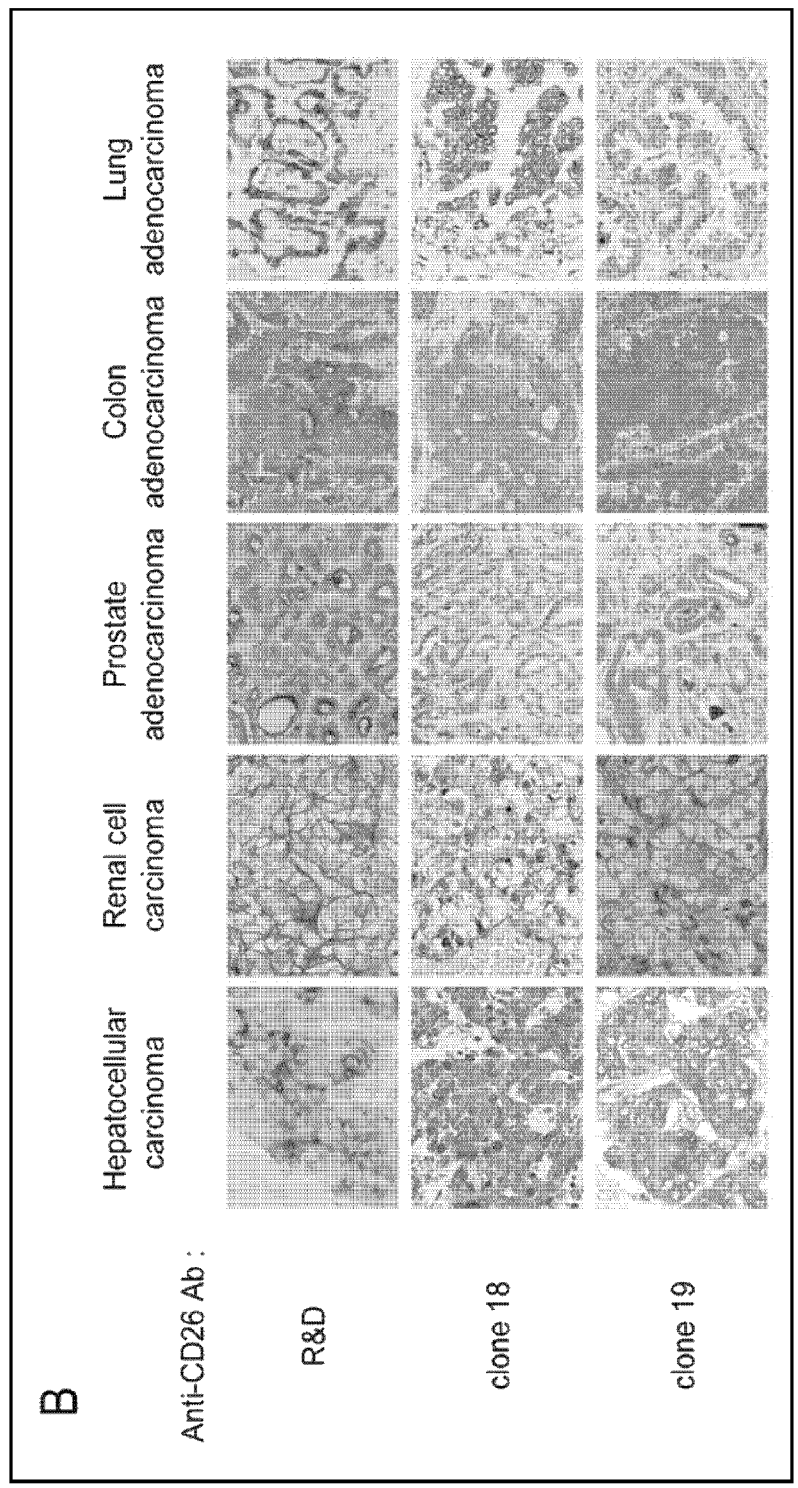

[Figure 3]
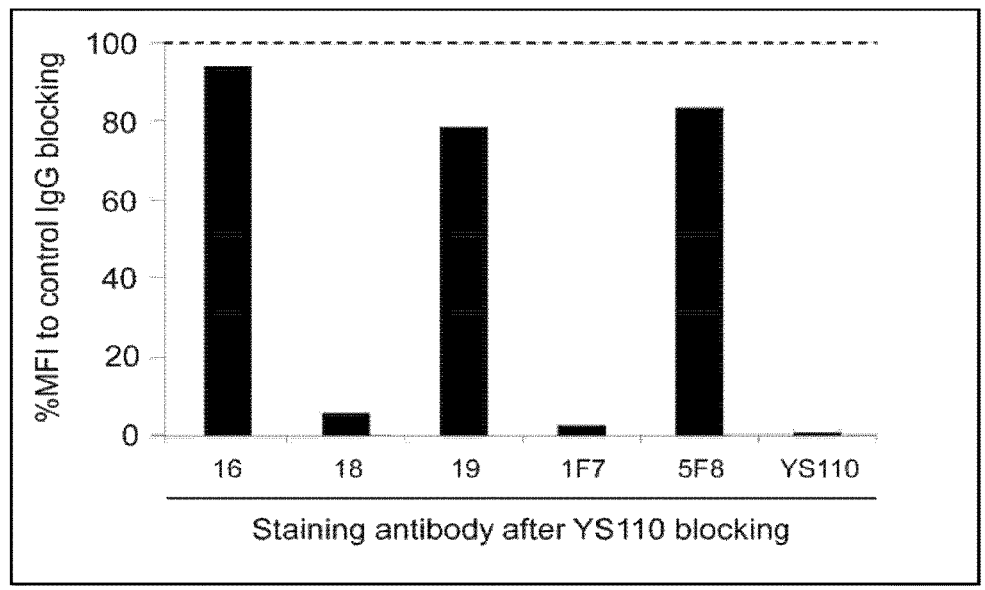
[Figure 4]
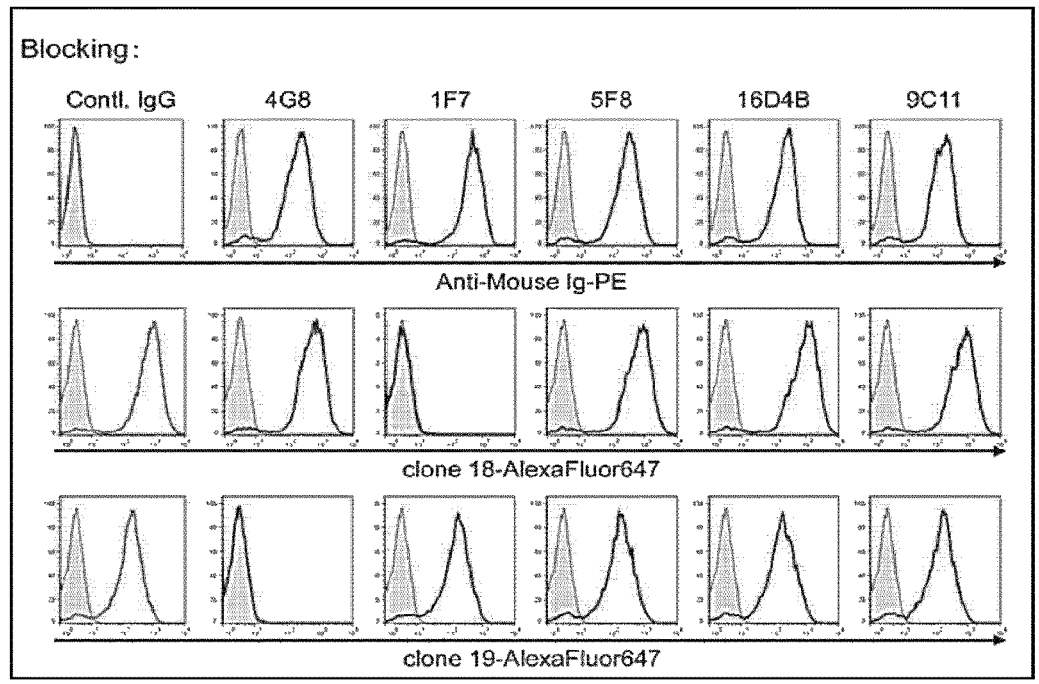

[Figure 5]
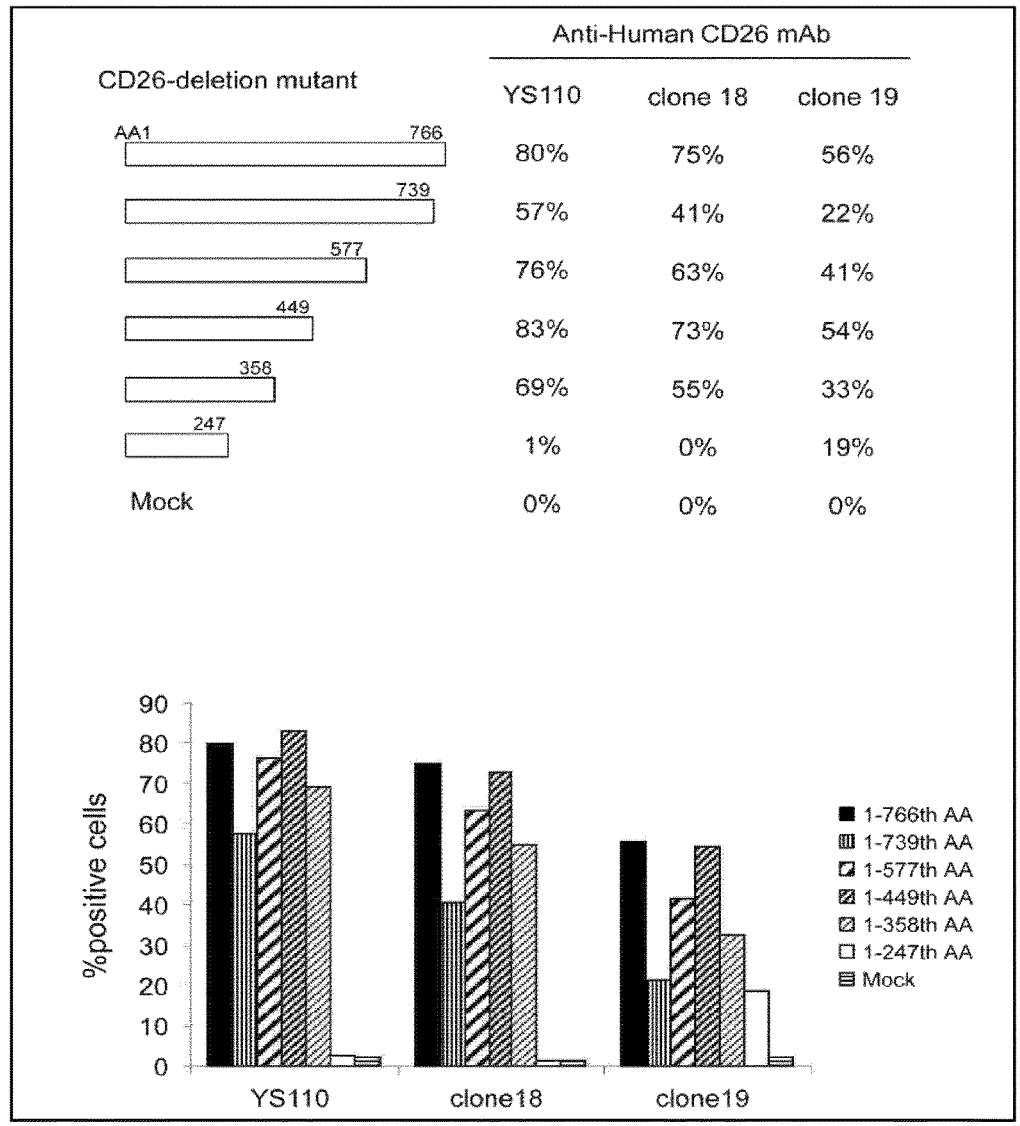

[Figure 6]
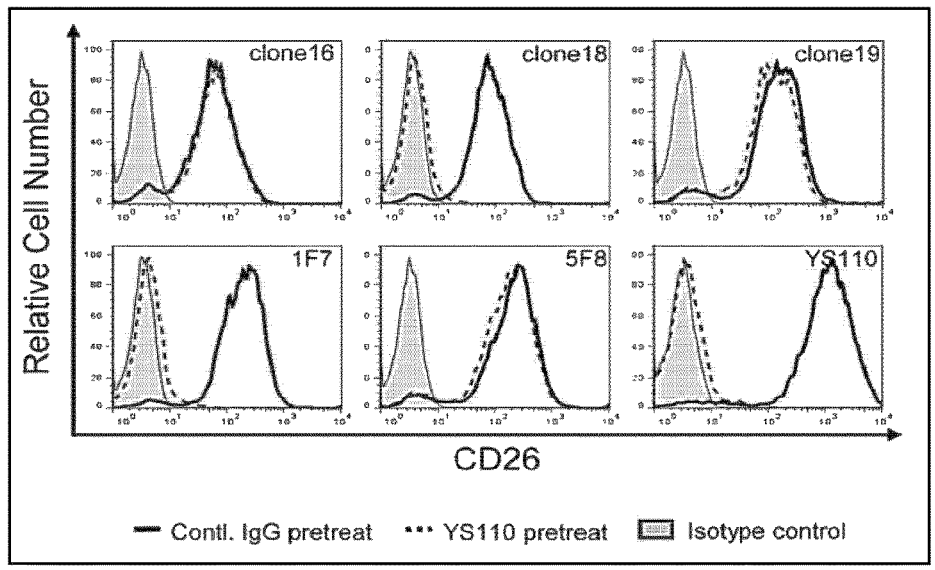
[Figure 7]
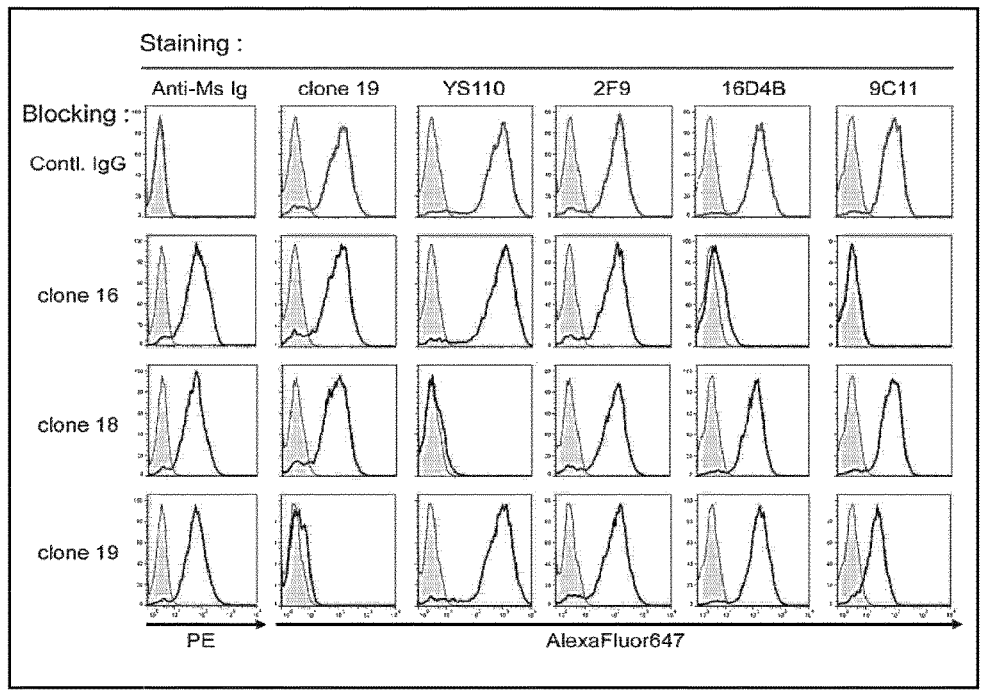

[Figure 8]
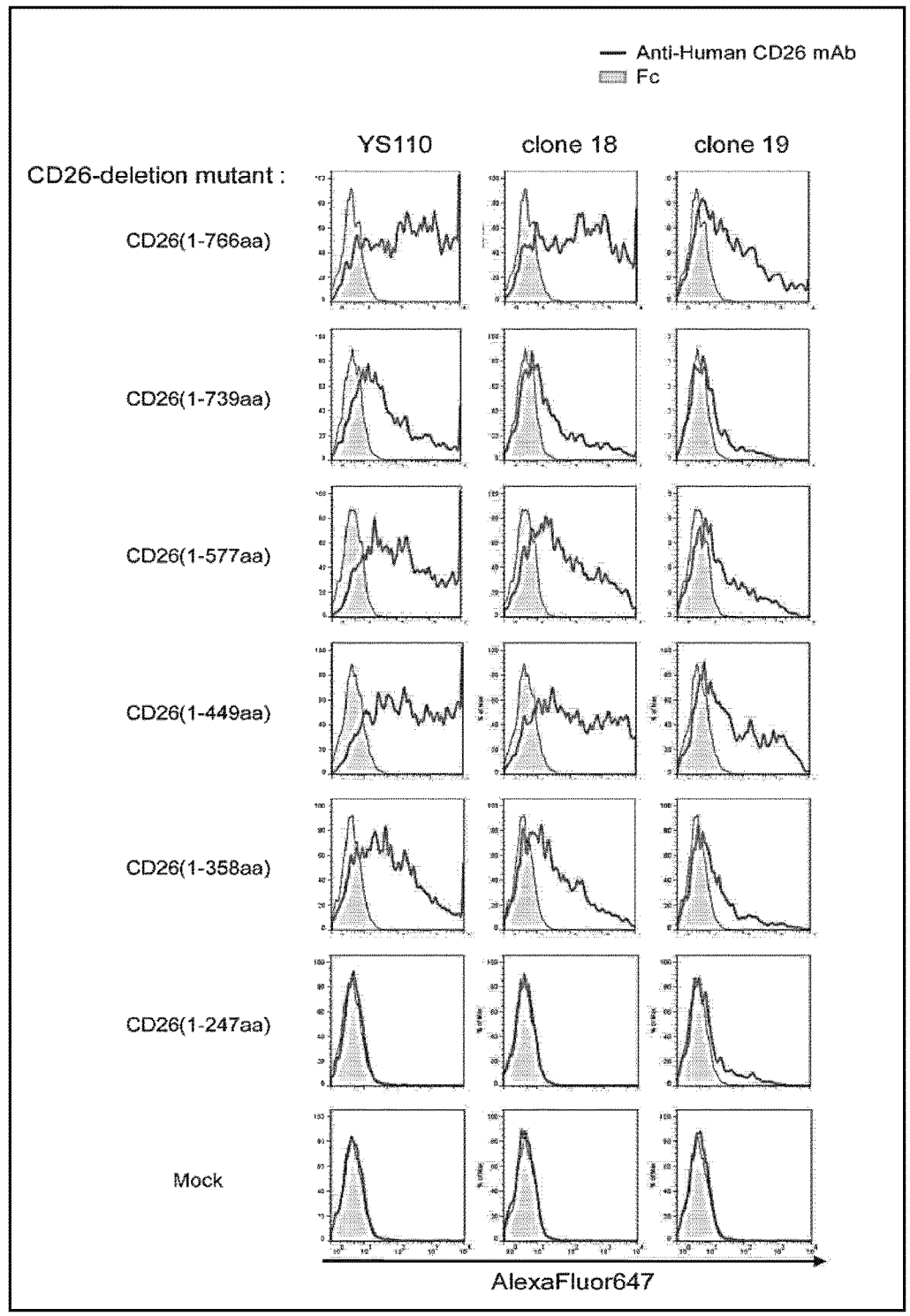

SEQUENCE LISTING

```
<160> NUMBER OF SEQ ID NOS: 1

<210> SEQ ID NO 1
<211> LENGTH: 766
<212> TYPE: PRT
<213> ORGANISM: human

<400> SEQUENCE: 1

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255
```

```
Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
    370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
    530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
        595                 600                 605

Ala Ala Arg Gln Phe Ser Lys Met Gly Phe Val Asp Asn Lys Arg Ile
    610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
```

-continued

|   |   |   | 675 |   |   |   |   | 680 |   |   |   |   | 685 |   |   |
|---|---|---|---|---|---|---|---|---|---|---|---|---|---|---|---|
| Met | Ser | Arg | Ala | Glu | Asn | Phe | Lys | Gln | Val | Glu | Tyr | Leu | Leu | Ile | His |
|   |   | 690 |   |   |   | 695 |   |   |   |   | 700 |   |   |   |   |
| Gly | Thr | Ala | Asp | Asp | Asn | Val | His | Phe | Gln | Gln | Ser | Ala | Gln | Ile | Ser |
| 705 |   |   |   |   | 710 |   |   |   |   | 715 |   |   |   |   | 720 |
| Lys | Ala | Leu | Val | Asp | Val | Gly | Val | Asp | Phe | Gln | Ala | Met | Trp | Tyr | Thr |
|   |   |   |   | 725 |   |   |   |   | 730 |   |   |   |   | 735 |   |
| Asp | Glu | Asp | His | Gly | Ile | Ala | Ser | Ser | Thr | Ala | His | Gln | His | Ile | Tyr |
|   |   |   | 740 |   |   |   |   | 745 |   |   |   |   | 750 |   |   |
| Thr | His | Met | Ser | His | Phe | Ile | Lys | Gln | Cys | Phe | Ser | Leu | Pro |   |   |
|   |   | 755 |   |   |   |   | 760 |   |   |   |   | 765 |   |   |   |

ANTI-HUMAN CD26 MONOCLONAL ANTIBODY OR ANTIGEN-BINDING FRAGMENT THEREOF

TECHNICAL FIELD

The present invention relates to an anti-human CD26 monoclonal antibody or an antigen-binding fragment thereof, etc.

BACKGROUND ART

Human CD26 has been reported as a human peripheral blood T-cell surface antigen which reacts with a mouse monoclonal antibody Tal, and then established as a T-cell activation antigen because of being strongly expressed on activated T-cells (Non Patent Literatures 1 and 2). On the other hand, peptidase enzyme activity had previously been known to exist in the liver or on the cell surface of the intestinal mucosa and studied as dipeptidyl peptidase IV (DPPIV). In 1992, DPPIV and CD26 were found identical by gene cloning (Non Patent Literature 2). CD26 is composed of 766 amino acids and is a so-called type II membrane glycoprotein with its N terminus located in the cytoplasm (Non Patent Literature 3). Only 6 amino acid residues are located in the cytoplasm, while an existing signal-related motif structure is absent. Although the average molecular weight of CD26 predicted from the amino acid sequence is approximately 88 kDa, CD26 is detected as a glycoprotein of approximately 110 kDa in vivo because a region of 48 to 324 residues undergoes sugar chain modification. CD26 has the enzyme activity of a serine protease DPPIV with an active-site serine residue at position 630 and cleaves the C-terminal side of proline or alanine at position 2 counting from the N terminus of a substrate peptide.

CD26 is strongly expressed on memory T-cells in peripheral blood lymphocytes (Non Patent Literatures 4 and 5). Flow cytometry study on the expression of CD26 on resting T-cells shows 3-phase patterns as the expression intensity thereof, which can be divided into 3 populations: a population highly expressing CD26 (referred to as $CD26^{high}$ or $CD26^{bright}$); a population moderately expressing CD26 (referred to as $CD26^{int}$ or $CD26^{intermediate}$); and a population expressing no CD26 (referred to as $CD26^{negative}$). In this context, the $CD26^{high}$ population is considered to play a particularly important role in immune response (Non Patent Literature 4). The $CD26^{high}$ population belongs to memory T-cells expressing CD45RO and reacts with a memory antigen such as tetanus toxoid, further induces the antibody production of B cells, and also has the activity of inducing MHC class I-specific killer T-cells (Non Patent Literature 4). The CD26-positive T-cells are $T_H1$ cells, which secrete cytokines such as IL-2 or IFN-γ. These cells have migration activity between vascular endothelial cells and are considered to play an important role in local inflammation by migrating and accumulating at the inflammation site (Non Patent Literatures 3, 6, and 7).

The present inventors have found that co-stimulation with CD26 in CD8-positive T-cells also controls cytotoxic activity (Non Patent Literature 8). The present inventors have further used models with xenogeneic GVHD (graft versus host disease) developed by the transplantation of human peripheral blood mononuclear cells to NOD/Shi-scid-IL2Rγ$^{null}$ mice (NOG mice) and found that the activation control of T-cells by an anti-human CD26 humanized antibody is very effective for the prevention or treatment of GVHD (Non Patent Literature 9). CD26 is also expressed in various cancers, for example, lung cancer, colorectal cancer, malignant mesothelioma, kidney cancer, prostate cancer, thyroid gland cancer, gastrointestinal stromal tumor (GIST), T-cell malignant lymphoma, and glioma (Non Patent Literature 10). CD26-positive gastrointestinal stromal tumor (GIST) patients have also been reported to have a very poor prognosis (Non Patent Literature 11).

The present inventors have reported that an antibody against CD26 exerts a very effective antitumor effect on kidney cancer, malignant mesothelioma, malignant lymphoma, and the like, and developed an anti-human CD26 humanized antibody YS110, which is under phase I clinical trial targeting CD26-positive malignant mesothelioma and other CD26-positive tumors in France (anti-human CD26 humanized antibody therapy) (Patent Literature 1 and Non Patent Literatures 12 and 13).

CITATION LIST

Patent Literature

Patent Literature 1: WO 2008/114876

Non Patent Literature

Non Patent Literature 1: Fox D A, Hussey R E, Fitzgerald K A, et al. (1984) Tal, a novel 105 K D human T cell activation antigen defined by a monoclonal antibody. J Immunol 133: 1250-1256

Non Patent Literature 2: Tanaka T, Camerini D, Seed B, et al. (1992) Cloning and functional expression of the T cell activation antigen CD26. J Immunol 149: 481-486

Non Patent Literature 3: Ohnuma K, Dang N H, Morimoto C (2008) Revisiting an old acquaintance: CD26 and its molecular mechanisms in T cell function. Trends in immunology 29: 295-301

Non Patent Literature 4: Morimoto C, Schlossman S F (1998) The structure and function of CD26 in the T-cell immune response. Immunol Rev 161: 55-70

Non Patent Literature 5: Dang N H, Torimoto Y, Sugita K, et al. (1990) Cell surface modulation of CD26 by anti-1F7 monoclonal antibody. Analysis of surface expression and human T cell activation. J Immunol 145: 3963-3971

Non Patent Literature 6: Masuyama J, Yoshio T, Suzuki K, et al. (1999) Characterization of the 4C8 antigen involved in transendothelial migration of $CD26^{hi}$ T cells after tight adhesion to human umbilical vein endothelial cell monolayers. J Exp Med 189: 979-990

Non Patent Literature 7: Ohnuma K, Inoue H, Uchiyama M, et al. (2006) T-cell activation via CD26 and caveolin-1 in rheumatoid synovium. Mod Rheumatol 16: 3-13

Non Patent Literature 8: Hatano R, Ohnuma K, Yamamoto J, Dang N H, Morimoto C (2013) CD26-mediated co-stimulation in human CD8$^+$ T cells provokes effector function via pro-inflammatory cytokine production. Immunology 138: 165-172

Non Patent Literature 9: Hatano R, Ohnuma K, Yamamoto J, Dang N H, Yamada T, Morimoto C (2013) Prevention of acute graft-versus-host disease by humanized anti-CD26 monoclonal antibody. Br J Haematol 162: 263-277

Non Patent Literature 10: Havre P A, Abe M, Urasaki Y, Ohnuma K, Morimoto C, Dang N H (2008) The role of CD26/dipeptidyl peptidase IV in cancer. Front Biosci 13: 1634-1645

Non Patent Literature 11: Umio Yamaguchi, et al. (2008) Distinct Gene Expression-Defined Classes of Gastrointestinal Stromal Tumor. Journal of Clinical Oncology vol. 26, number 25, 4100-4108

Non Patent Literature 12: Inamoto T, Yamada T, Ohnuma K, et al. (2007) Humanized anti-CD26 monoclonal antibody as a treatment for malignant mesothelioma tumors. Clin Cancer Res 13: 4191-4200

Non Patent Literature 13: Aoe K, Amatya V J, Fujimoto N, et al. (2012) CD26 overexpression is associated with prolonged survival and enhanced chemosensitivity in malignant pleural mesothelioma. Clin Cancer Res 18: 1447-1456

SUMMARY OF INVENTION

Problems to be Solved by the Invention

In order to predict the efficacy or adverse effects of a therapeutic agent, movements toward the early development, together with the therapeutic agent, of a diagnostic agent for use in a set with the therapeutic agent (also referred to as a so-called "companion diagnostic agent") have become active in recent years. The companion diagnostic agent can be utilized for diagnosing the expression of a target molecule, the presence or absence of a mutation, a polymorphism in a drug-metabolizing enzyme, etc. As for treatment using an anti-human CD26 humanized antibody, it is also desirable to conduct analysis etc., of the expression of CD26 in cancer tissues, immune tissues, or the like, for example, in order to select a patient applicable to treatment or to monitor therapeutic effects. There is the need for the development of an anti-human CD26 antibody which permits such analysis, etc., and can also be used in immunostaining.

Unfortunately, mouse anti-human CD26 monoclonal antibodies previously developed by the present inventors (4G8, 1F7, 5F8, 2F9, 16D4B, and 9C11 (for the details of these clones, see the present Examples)) cannot be used in immunostaining.

As a result of studying various commercially available anti-human CD26 monoclonal antibodies as research reagents for immunostaining, mouse anti-human CD26 monoclonal antibody clone 44-4 from MBL (Medical & Biological Laboratories Co., Ltd.) (catalog No. D068-1) was found unreliable because this antibody did not exhibit distinct staining properties in the immunostaining and varied in stained positions.

On the other hand, as a result of studying commercially available anti-human CD26 polyclonal antibodies, a goat anti-human CD26 polyclonal antibody from R&D Systems, Inc. (catalog No. AF1180) and a rabbit anti-human CD26 polyclonal antibody from Novus Biologicals, LLC (catalog No. NB100-59021) were found to exhibit distinct staining properties capable of meeting the clinical diagnosis of pathological tissues. Since these anti-human CD26 antibodies, however, are polyclonal antibodies, the major problem thereof is lot-to-lot variations. Specifically, staining using polyclonal antibodies might result in different staining intensity or staining patterns among the antibodies differing in lot. In this respect, use of polyclonal antibodies, for example, as clinical diagnostic agents, which are always required to produce a stable consequence, is not appropriate.

Means for Solving the Problems

The present inventors have conducted diligent studies and consequently completed the present invention by finding a novel anti-human CD26 monoclonal antibody which solves the problems mentioned above.

Specifically, an object of the present invention is attained by providing (1) An anti-human CD26 monoclonal antibody or an antigen-binding fragment thereof, binding to an epitope which is recognized by a monoclonal antibody produced by a hybridoma deposited under Accession No. NITE BP-01642, a hybridoma deposited under Accession No. NITE BP-01643, or a hybridoma deposited under Accession No. NITE BP-01644.

(2) According to one embodiment, for the anti-human CD26 monoclonal antibody or the antigen-binding fragment thereof according to (1), preferably, the anti-human CD26 monoclonal antibody or the antigen-binding fragment thereof has complementarity-determining regions of the monoclonal antibody produced by a hybridoma deposited under Accession No. NITE BP-01642, a hybridoma deposited under Accession No. NITE BP-01643, or a hybridoma deposited under Accession No. NITE BP-01644.

(3) According to one embodiment, for the anti-human CD26 monoclonal antibody or the antigen-binding fragment thereof according to (1) or (2), preferably, the anti-human CD26 monoclonal antibody is the monoclonal antibody produced by a hybridoma deposited under Accession No. NITE BP-01642, a hybridoma deposited under Accession No. NITE BP-01643, or a hybridoma deposited under Accession No. NITE BP-01644.

(4) According to one embodiment, for the anti-human CD26 monoclonal antibody or the antigen-binding fragment thereof according to any of (1) to (3), preferably, the anti-human CD26 monoclonal antibody or the antigen-binding fragment thereof does not substantially exhibit competition for binding with an anti-human CD26 humanized antibody YS110.

(5) In another aspect, the present invention provides a composition for detecting human CD26, comprising an anti-human CD26 monoclonal antibody or an antigen-binding fragment thereof according to any of (1) to (4).

(6) According to one embodiment, for the composition for detecting human CD26 according to (5), preferably, the detection of human CD26 is detection by immunostaining.

(7) According to one embodiment, for the composition for detecting human CD26 according to (6), preferably, the detection of human CD26 is performed for a fixed tissue preparation.

(8) According to one embodiment, for the composition for detecting human CD26 according to (7), preferably, the fixed tissue preparation is obtained by fixation by treatment with formalin and/or paraffin embedding.

(9) In a further aspect, the present invention provides a method for detecting human CD26, comprising the steps of:

contacting an anti-human CD26 monoclonal antibody or an antigen-binding fragment thereof according to any of (1) to (4) with a sample derived from a subject; and detecting human CD26, if present, in the sample by immunostaining.

(10) In a further aspect, the present invention provides
a method for determining the suitability of administration of an antibody for treatment of a human CD26-related disease for a patient having or suspected of having the human CD26-related disease, comprising the steps of:
contacting an anti-human CD26 monoclonal antibody or an antigen-binding fragment thereof according to any of (1) to (4) with a sample derived from a subject; and
detecting human CD26, if present, in the sample by immunostaining.
(11) According to one embodiment, for the determination method according to (10), preferably,
the determination method further comprises the step of determining the suitability of administration of an antibody for treatment of a human CD26-related disease according to the degree of detection of human CD26 in the immunostaining.
(12) According to one embodiment, for the determination method according to (10) or (11), preferably,
the human CD26-related disease is a cancer, an immune disease, a viral disease, or a metabolic disease.
(13) According to one embodiment, for the determination method according to (12), preferably
the cancer, the immune disease, the viral disease, or the metabolic disease is selected from the group consisting of malignant mesothelioma, liver cancer, kidney cancer, prostate cancer, colorectal cancer, lung cancer, thyroid gland cancer, I-cell malignant lymphoma, gastrointestinal stromal tumor (GIST), glioma, autoimmune disease, graft versus host disease (GVHD), disease caused by coronavirus, and diabetes mellitus.
(14) In a further aspect, the present invention provides
use of an anti-human CD26 monoclonal antibody or an antigen-binding fragment thereof according to any of (1) to (4) for the detection of human CD26.
(15) In a further aspect, the present invention provides
a hybridoma selected from the group consisting of a hybridoma deposited under Accession No. NITE BP-01642, a hybridoma deposited under Accession No. NITE BP-01643, and a hybridoma deposited under Accession No. NITE BP-01644.
One of or any combination of two or more of the features of the present invention mentioned above is included in the scope of the present invention, as a matter of course.

Effects of Invention

The anti-human CD26 monoclonal antibody of the present invention or the antigen-binding fragment thereof can be used in the detection of human CD26, preferably the detection of human CD26 by immunostaining, in a sample derived from a subject.

BRIEF DESCRIPTION OF DRAWINGS

FIG. 1 is a diagram showing screening results of the culture supernatant of each hybridoma containing an anti-human CD26 monoclonal antibody. FIG. 1A relates to results of primary screening by flow cytometry. The culture supernatant of each hybridoma clone was mixed with Jurkat-CD26WT, then stained with a secondary antibody (PE-labeled anti-mouse IgG antibody), and analyzed for binding to human CD26 by flow cytometer. In the diagram, the binding of typical clones to human CD26 is indicated by histogram. MFI is an abbreviation of mean fluorescence intensity and denotes a value (=an average value) determined by dividing the total sum of respective fluorescence intensities of all cells taken as data by the total number of cells. The abscissa of the histogram of flow cytometry depicts fluorescence intensity, and the ordinate thereof depicts the number of cells. Higher fluorescence intensity means that a larger number of molecules of the antibody against human CD26 are bound per one cell. FIG. 1B relates to results of secondary screening by enzyme-linked immunosorbent assay (ELISA). Undenatured soluble human CD26 (also referred to as "sCD26") and denatured soluble human CD26 treated with a urea buffer were each immobilized on a solid-phase plate, and the culture supernatant of each hybridoma clone was added to the plate for binding. Subsequently, a secondary antibody (horseradish peroxidase (HRP)-conjugated anti-mouse IgG antibody) was reacted therewith, and the absorbance (absorption wavelength) at 450 nm was measured with a plate reader. In the diagram, the results about typical clones are shown.

FIG. 2A is a diagram showing results of immunostaining of pathological tissues using the culture supernatant of each hybridoma clone or clone 44-4 from MBL (Medical & Biological Laboratories Co., Ltd.), or a purified polyclonal antibody from R&D Systems, Inc. This diagram shows the results of immunostaining of formalin-fixed human normal tissues (liver, kidney, and prostate tissues) expressing human CD26, and each formalin-fixed tissue preparation of malignant mesothelioma using the culture supernatant of each hybridoma clone.

FIG. 2B is a diagram showing results of immunostaining of pathological tissues using an IgG fraction purified from the culture supernatant of each hybridoma clone, or a purified polyclonal antibody from R&D Systems, Inc. This diagram shows the results of immunostaining of each formalin-fixed tissue preparation of hepatocellular carcinoma, renal cell carcinoma, prostate cancer, colon adenocarcinoma, and lung adenocarcinoma expressing human CD26 using the IgG fraction obtained by the purification of the culture supernatant of each hybridoma clone.

FIG. 3 is a diagram showing competition with an anti-human CD26 humanized antibody YS110. Jurkat-CD26WT was mixed with unlabeled YS110 or a control human IgG antibody. Then, the culture supernatant of each hybridoma clone was added to the mixture. Subsequently, the cells were stained with a secondary antibody (PE-labeled goat anti-mouse IgG antibody) and analyzed for binding to human CD26 by flow cytometer. Only in the case of the staining using YS110, YS110 labeled directly with Alexa Fluor® 647 was used. A higher numerical value of the ordinate means that competition with YS110 was less likely to occur.

FIG. 4 shows results of analyzing an antigen-binding site in an anti-human CD26 monoclonal antibody produced by obtained clone 18 or clone 19, using a flow cytometer. Jurkat-CD26WT was mixed with each unlabeled anti-human CD26 monoclonal antibody (4G8, 1F7, 5F8, 16D4B, and 9C11) or a control mouse $IgG_1$ antibody. Subsequently, the cells were stained with a purified IgG antibody (derived from the culture supernatant of clone 18 or clone 19) labeled directly with Alexa Fluor® 647 or a PE-labeled anti-mouse IgG antibody (Anti-Mouse Ig-PE) and then analyzed for binding to human CD26 by flow cytometer.

FIG. 5 is a diagram showing the binding of the obtained anti-human CD26 monoclonal antibody of the present invention to human CD26-deletion mutants. Full-length human CD26 and 5 types of human CD26-deletion mutants were each expressed in COS-7 cells. Subsequently, the cells were stained with an anti-human CD26 humanized antibody YS110 or a purified IgG antibody (derived from the culture supernatant of clone 18 or clone 19) labeled directly with Alexa Fluor® 647 and then analyzed for binding to the full-length human CD26 or the human CD26-deletion mutants by flow cytometer. The number indicates the ratio of the number of Alexa Fluor® 647-positive cells to the total number of cells taken as data by %.

FIG. 6 is a diagram showing competition with an anti-human CD26 humanized antibody YS110. Jurkat-CD26WT was mixed with unlabeled YS110 or a control human IgG antibody. Then, the culture supernatant of each hybridoma clone was added to the mixture. Subsequently, the cells were stained with a secondary antibody (PE-labeled anti-mouse IgG antibody) and then analyzed for binding to human CD26 by flow cytometer. Only in the case of the staining using YS110, YS110 labeled directly with Alexa Fluor® 647 was used. In the diagram, the binding to human CD26 is indicated by histogram.

FIG. 7 is a diagram showing the competition of the obtained anti-human CD26 monoclonal antibody of the present invention with various anti-CD26 monoclonal antibodies. Jurkat-CD26WT was mixed with the culture supernatant of each hybridoma clone (clone 16, clone 18, and clone 19) or a control mouse $IgG_1$ antibody, then stained with an anti-human CD26 humanized antibody YS110 or each anti-human CD26 monoclonal antibody (2F9, 16D4B, 9C11, and a purified IgG antibody from the culture supernatant of clone 19) labeled directly with Alexa Fluor® 647, or a PE-labeled anti-mouse IgG antibody, and then analyzed for binding to human CD26 by flow cytometer. In the diagram, the binding to human CD26 is indicated by histogram.

FIG. 8 is a diagram showing the binding of the obtained anti-human CD26 monoclonal antibody of the present invention to human CD26-deletion mutants. Full-length human CD26 and 5 types of human CD26-deletion mutants were each expressed in COS-7 cells. Subsequently, the cells were stained with an anti-human CD26 humanized antibody YS110 or a purified IgG antibody (derived from the culture supernatant of clone 18 or clone 19) labeled directly with Alexa Fluor® 647 and then analyzed for binding to the full-length human CD26 or the human CD26-deletion mutants by flow cytometer. In the diagram, the binding to human CD26 is indicated by histogram.

DESCRIPTION OF EMBODIMENTS

In the present specification, the antibody may refer to an immunoglobulin molecule capable of specifically binding to a target such as a carbohydrate, a polynucleotide, a lipid, or a polypeptide via at least one antigen recognition site positioned in the variable regions of the immunoglobulin molecule. The antibody may refer to a whole polyclonal antibody or monoclonal antibody. The antigen-binding fragment is not particularly limited as long as the antigen-binding fragment is a functional and structural fragment of the antibody and maintains binding activity against an antigen to which the antibody can bind. Examples of the antigen-binding fragment include, but are not limited to, Fab, Fab', F(ab')$_2$, Fv, single-chain Fv (ScFv), their mutants, fusion proteins containing an antibody moiety, and other modified constructs of immunoglobulin molecules containing an antigen recognition site. The antibody can be of any class such as IgG, IgA, or IgM (or subclass thereof) and is not limited by a particular class. Immunoglobulins are classified into different classes depending on the amino acid sequences of their antibody heavy chain constant domains. There are five main immunoglobulin classes: IgA, IgD, IgE, IgG, and IgM, some of which can be further subdivided into, for example, subclasses (isotypes) $IgG_1$, $IgG_2$, $IgG_3$, $IgG_4$, $IgA_1$, and $IgA_2$. The heavy chain constant domains corresponding to the different classes of immunoglobulins are called α, δ, ε, γ and μ, respectively.

According to one embodiment, the anti-human CD26 monoclonal antibody of the present invention is an IgG antibody and may be, for example, an $IgG_1$ antibody or an $IgG_2$ antibody.

The variable regions of the antibody may mean the variable region of an antibody light chain and/or the variable region of an antibody heavy chain. The variable regions of the heavy chain and the light chain are each composed of 4 framework regions (FRs) linked by 3 complementarity-determining regions (CDRs) also known as hypervariable regions. CDRs in each chain are held in close proximity by FRs and contribute, together with CDRs in the other chain, to the formation of the antigen-binding site of the antibody. Examples of techniques for determining CDRs include, but are not limited to: (1) an approach based on cross-species sequence variability (e.g., Kabat et al., Sequences of Proteins of Immunological Interest, 5th ed., 1991, National Institutes of Health, Bethesda Md.); and (2) an approach based on the crystallographic study of an antigen-antibody complex (Al-lazikani et al., 1997 J. Molec. Biol. 273: 927-948). These two approaches may be used in combination.

The constant regions of the antibody may mean the constant region of an antibody light chain and/or the constant region of an antibody heavy chain.

The term "specifically binding" is a term well known to those skilled in the art, and a method for determining the specific binding of the antibody or the like to an antigen or an epitope is also well known. It should be understood that, for example, an antibody or an antigen-binding fragment thereof specifically binding to an epitope in CD26 is capable of binding to this epitope in CD26 more rapidly and/or for a longer duration with larger affinity and binding activity than its binding to other epitopes or non-epitope portions. However, the specific binding to a second target of an antibody or an antigen-binding fragment thereof specifically binding to a first target is not excluded therefrom.

The monoclonal antibody may mean an antibody which is obtained from a population of substantially homogeneous antibodies. Specifically, individual antibodies contained in the population are identical except for natural mutants that might be present to some extent. The monoclonal antibody is directed to a single antigen site and is very specific. In contrast to a typical polyclonal antibody targeting different antigens or different epitopes, each monoclonal antibody targets a single epitope in an antigen. The modifier "monoclonal" denotes the characteristics of the antibody which is obtained from a population of substantially homogeneous antibodies, and should not be restrictively interpreted as requiring the production of the antibody by a particular method.

The immunostaining refers to a histological (histochemical) approach of detecting an antigen in a tissue preparation using an antibody or a fragment thereof, and is a staining method for visualizing a particular antigen using an antibody which recognizes the antigen, and observing the localization thereof under an optical microscope or an electron microscope or the like. In the present specification, the term "immunostaining" may be used interchangeably with immunohistological staining or immunohistochemistry (IHC).

The anti-human CD26 monoclonal antibody of the present invention or the antigen-binding fragment thereof may be a chimeric antibody, a humanized antibody, a human antibody, an antibody of a nonhuman mammal (e.g., a mouse, a rat, a rabbit, cattle, a horse, or a goat), or an antigen-binding fragment thereof. According to one embodiment, an antibody of a nonhuman mammal is preferred. The chimeric antibody may refer to an antibody comprising only the variable regions of a nonhuman (e.g., mouse) antibody joined to the constant regions of a human antibody, and the resulting antibody has nonhuman-derived variable regions and human-derived constant regions. The humanized antibody may refer to an antibody in which only hypervariable regions (also referred to as complementarity-determining regions), which are moieties binding directly to an antigen, are of nonhuman (e.g., mouse) type. The human antibody may refer to an antibody which is obtained by: mating a nonhuman (e.g., mouse) immunoglobulin gene-knockout nonhuman animal (e.g., mouse) with a human immunoglobulin gene-transfected nonhuman animal to prepare a nonhuman animal producing only the human immunoglobulin; and preparing the human antibody from this nonhuman animal producing the human immunoglobulin.

The anti-human CD26 monoclonal antibody of the present invention or the antigen-binding fragment thereof may be in the form of a monomer, a dimer, or a multimer in some cases.

The anti-human CD26 monoclonal antibody of the present invention can be produced by various methods. Methods for producing monoclonal antibodies are well known to those skilled in the art (see e.g., Sambrook, J et al., Molecular Cloning, Cold Spring Harbor Laboratory Press (1989)).

The anti-human CD26 monoclonal antibody of the present invention can be produced by use of a hybridoma method as described in, for example, "Kohler and Milstein, 1975, Nature 256: 495" well known to those skilled in the art. In the hybridoma method, for example, a mouse, a hamster, or any of other suitable host animals can be immunized (sensitized) with the antigen (human) CD26 or a fragment thereof or the like to thereby allow the host animal to yield cells producing an antibody specifically binding to the antigen (antibody-producing cells). In order to enhance the antibody titer, for example, a complete Freund's adjuvant (CFA), a lipid adjuvant, a glucan polysaccharide adjuvant, an aluminum hydroxide adjuvant, or a synthetic copolymer adjuvant may be added thereto. Since the antibody-producing cells are mostly present in the spleen, splenocytes are generally isolated from the spleen and then immortalized by cell fusion with tumor cells (e.g., myeloma cells of a HGPRT (hypoxanthine-guanine phosphoribosyltransferase) enzyme-deficient 9-azaguanine-resistant line) to prepare hybridomas. The cell fusion can be performed using Sendai virus, polyethylene glycol, or electric stimulation or the like. The hybridomas thus prepared can be cultured in, for example, a HAT (hypoxanthine, aminopterin, and thymidine) medium to thereby select hybridomas of the splenocytes and the tumor cells. The selected hybridomas can be reseeded at one cell/well to obtain a hybridoma producing the anti-human CD26 monoclonal antibody. The culture supernatant may be further purified into, for example, an IgG fraction (IgG antibody), by use of an ammonium sulfate precipitation method, a gel filtration method, an ion-exchange chromatography method, or a protein A/G chromatography method or the like.

As for the antigen (CD26 or a fragment thereof, etc.) for use in the immunization, because human CD26 is composed of 766 amino acids with only its N-terminal 6 amino acid residues located in the cytoplasm, the human CD26 may be rendered soluble by preparing a mutated protein from which at least all of these amino acid residues located in the cytoplasm have been deleted (e.g., N-terminal amino acid residues 3 to 9 of human CD26 have been deleted). This mutated protein (soluble human CD26) can be secreted into a culture supernatant by integrating a DNA encoding the mutated protein into an appropriate expression vector and transfecting *E. coli* cells, monkey COS cells, or Chinese hamster ovary (CHO) cells or the like with the expression vector. Then, the mutated protein can be appropriately purified by chromatography or the like.

According to one embodiment, the purified soluble human CD26 may be treated by denaturation at, for example, 4° C. to 37° C., for 5 to 8 hours using a denaturant, for example, a urea buffer (e.g., 8 M urea, 20 mM HEPES, and 50 mM DTT), guanidine salt (e.g., 6 M guanidine hydrochloride), or sodium dodecyl sulfate (SDS) (e.g., 1% SDS), and then used in the immunization. Those skilled in the art can appropriately set the time, conditions, etc., required for the denaturation. For the denaturation treatment of the antigen with a urea buffer, see, for example, "Torigoe T. at al., (2012) Establishment of a monoclonal anti-pan HLA class I antibody suitable for immunostaining of formalin-fixed tissue: usually high frequency of down-regulation in breast cancer tissue. Pathology International 62; 303-308".

According to one embodiment, the anti-human CD26 monoclonal antibody of the present invention or the antigen-binding fragment thereof can be an anti-human CD26 monoclonal antibody produced from, for example, the hybridoma of the present invention (i.e., clone 19 (Accession No. NITE BP-01642), clone 18 (Accession No. NITE BP-01643), or clone 16 (Accession No. NITE BP-01644), which is a hybridoma deposited with the Patent Microorganisms Depositary of the National Institute of Technology and Evaluation (NITE) (2-5-8, Kazusakamatari, Kisarazu, Chiba, Japan); deposition date: Jul. 3, 2013 for all of these hybridomas), or an antigen-binding fragment thereof. Alternatively, the anti-human CD26 monoclonal antibody of the present invention or the antigen-binding fragment thereof can be an anti-human CD26 monoclonal antibody or an antigen-binding fragment thereof binding to an epitope which is recognized (bound) by the monoclonal antibody produced by any of these hybridomas. Preferably, the monoclonal antibody produced by any of these hybridomas and the anti-human CD26 monoclonal antibody or the antigen-binding fragment thereof binding to an epitope which is recognized by this antibody recognize and bind to substantially or totally the same epitope. Substantially the same epitope may refer to an epitope having an amino acid modification, substitution, addition, deletion, or the like that does not influence the binding activity of the antibody or the antigen-binding fragment thereof. Alternatively, an anti-human CD26 monoclonal antibody or an antigen-binding fragment thereof having complementarity-determining regions of the monoclonal antibody produced by any of these hybridomas is also included in the scope of the present invention. Preferably, the monoclonal antibody produced by any of these hybridomas and the anti-human CD26 monoclonal antibody or the antigen-binding fragment thereof having complementarity-determining regions of this antibody have substantially or totally the same complementarity-determining regions. Substantially the same complementarity-determining regions may refer to complementarity-determining regions having an amino acid modification, substitution, addition, deletion, or the like that does not influence the binding activity of the antibody or the antigen-binding fragment thereof.

Alternatively, the anti-human CD26 monoclonal antibody of the present invention or the antigen-binding fragment thereof may be prepared by a gene recombination technique as described in, for example, U.S. Pat. No. 4,816,567. Alternatively, the anti-human CD26 monoclonal antibody of the present invention or the antigen-binding fragment thereof may be prepared by a phage display technique (e.g., U.S. Pat. Nos. 5,565,332, 5,580,717, 5,733,743, and 6,265, 150). A DNA encoding the anti-human CD26 monoclonal antibody of the present invention or the antigen-binding fragment thereof can be isolated and sequenced by conventional methods such as use of an oligonucleotide probe capable of specifically binding to a gene encoding a heavy chain or a light chain of the monoclonal antibody. The DNA thus isolated may be integrated into an expression vector, and host cells such as E. coli cells, monkey COS cells, Chinese hamster ovary (CHO) cells, or myeloma cells which produce immunoglobulin proteins only when the expression vector is transferred thereto, can be transfected with the expression vector to thereby allow the host cells to produce the anti-human CD26 monoclonal antibody of the present invention or the antigen-binding fragment thereof.

The antigen-binding fragment of the anti-human CD26 monoclonal antibody of the present invention is not particularly limited as long as the antigen-binding fragment is a functional and structural fragment of the antibody and maintains binding activity against an antigen to which the antibody can bind. Examples of the antigen-binding fragment include Fab, Fab', F(ab')$_2$, Fv, single-chain Fv (ScFv), their mutants, fusion proteins containing an antibody moiety, bispecific antibodies, and other modified constructs of immunoglobulin molecules containing an antigen recognition site. These antibody-binding fragments may be produced by a gene recombination technique or a chemical synthesis technique or the like based on production methods generally known to those skilled in the art.

The antigen-binding fragment can be obtained, for example, via the protein digestion of a whole antibody (e.g., Morimoto et al., 1992, J. Biochem. Biophys. Methods 24: 107-117), or may be produced directly by recombinant host cells (e.g., a eukaryote such as yeast cells, plant cells, insect cells, or mammal cells, or a prokaryote such as E. coli). For example, Fab'-SH fragments may be recovered directly from E. coli and chemically bound to each other to form a F(ab')$_2$ fragment (Carter et al., 1992, Bio/Technology 10: 163-167). Alternatively, F(ab')$_2$ may be formed using a leucine zipper GCN4, which promotes the assembly of a F(ab')$_2$ molecule. In the case of producing scFv by a chemical synthesis technique, an automatic synthesizer can be used. In the case of producing scFv by a gene recombination technique, a suitable plasmid containing a polynucleotide encoding the scFv can be transferred to suitable host cells (e.g., an eukaryote such as yeast cells, plant cells, insect cells, or mammal cells, or a prokaryote such as E. coli). The polynucleotide encoding the scFv of interest may be prepared by a well-known operation such as polynucleotide ligation. The resulting scFv may be isolated by use of a standard protein purification technique known in the art.

The anti-human CD26 monoclonal antibody of the present invention or the antigen-binding fragment thereof may be modified, if desired. The substantial modification based on the biological characteristics of the antibody can be achieved by a modification (e.g., substitution, deletion, or addition of amino acid residues) which changes, for example, (a) the three-dimensional structure of an amino acid sequence in a modification region, such as a sheet or helix conformation; (b) the status of electric charge or hydrophobicity of the molecule at a target site; or (c) the effects of the modification on the maintenance of the volume of a side chain.

In the present specification, the amino acid is used in the broadest sense thereof and includes not only natural amino acids, for example, serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and praline (Pro) but also nonnatural amino acids such as amino acid mutants and derivatives. Those skilled in the art naturally understand, by taking this wide definition into consideration, that examples of the amino acid in the present specification include: L-amino acids; D-amino acids; chemically modified amino acids such as amino acid mutants and amino acid derivatives; amino acids, such as norleucine, β-alanine, and ornithine, which do not serve as materials constituting proteins in vivo; and chemically synthesized compounds having the characteristics of amino acids generally known to those skilled in the art. Examples of the nonnatural amino acids include α-methylamino acids (α-methylalanine, etc.), D-amino acids (D-aspartic acid, D-glutamic acid, etc.), histidine-like amino acids (2-amino-histidine, β-hydroxy-histidine, homohistidine, α-fluoromethyl-histidine, α-methyl-histidine, etc.), amino acids having extra methylene in their side chains ("homo" amino acids), and amino acids in which a carboxylic acid functional group in the side chain is substituted by a sulfonic acid group (cysteic acid, etc.).

For example, naturally occurring amino acid residues can be classified into the following groups based on general side chain characteristics:
(1) hydrophobic residues: Met, Ala, Val, Leu, and Ile;
(2) neutral hydrophilic residues: Cys, Ser, and Thr;
(3) acidic residues: Asp and Glu;
(4) basic residues: Asn, Gln, His, Lys, and Arg;
(5) residues influencing chain orientation: Gly and Pro; and
(6) aromatic residues: Trp, Tyr, and Phe.

The non-conservative substitution of an amino acid sequence constituting the antibody or the antigen-binding fragment thereof may be performed by replacing an amino acid belonging to one of these groups with an amino acid belonging to any of other groups. More conservative substitution may be performed by replacing an amino acid belonging to one of these groups with another amino acid belonging to the same group. Likewise, the deletion or the substitution in an amino acid sequence may be appropriately performed.

An arbitrary cysteine residue which does not participate in the maintenance of a suitable three-dimensional structure of the antibody may be substituted (usually, by serine) to thereby improve the oxidative stability of the molecule and prevent its abnormal cross-linking. On the contrary, when the antigen-binding fragment is an antibody fragment such as an Fv fragment, a cysteine bond can be added to the antigen-binding fragment to thereby improve the stability of the antigen-binding fragment.

The modification of amino acid(s) constituting the antibody or the antigen-binding fragment thereof may be the alteration or modification of one or more amino acids or may be the complete redesign of a region such as a variable region. The alternation of the variable region may change binding affinity and/or specificity. According to one embodiment, 1 to 5 or less conservative amino acid substitutions may be performed on CDRs. According to another embodiment, 1 to 3 or less conservative amino acid substitutions may be performed on CDR3. According to a further embodiment, the CDRs may be CDRH3 and/or CDRL3.

The modification of amino acid(s) constituting the antibody or the antigen-binding fragment thereof may be, for example, a posttranslational modification such as glycosylation with a sugar, acetylation, or phosphorylation. The antibody may be glycosylated at a conserved position in its constant region. The glycosylation of the antibody is usually of N-linked or O-linked type. The N-linked glycosylation means the binding of a carbohydrate moiety to the side chain of an asparagine residue. Tripeptide sequences asparagine-X-serine, asparagine-X-threonine, and asparagine-X-cysteine (wherein X is any amino acid other than proline) are recognition sequences for enzymatically adding a carbohydrate moiety to the asparagine side chain. Any of these tripeptide sequences is present in the antibody or the antigen-binding fragment thereof so that a potential glycosylation site is present. The O-linked glycosylation may be the binding of N-acetylgalactosamine, galactose, or xylose to a hydroxyamino acid (e.g., serine or threonine), or may be the binding thereof to 5-hydroxyproline or 5-hydroxylysine in some cases. Those skilled in the art can appropriately select the glycosylation conditions (in the case of performing the glycosylation by use of a biological approach, for example, host cells and the type and pH of a cell medium) according to the purpose.

The anti-human CD26 monoclonal antibody of the present invention or the antigen-binding fragment thereof can be further modified by using other modification methods alone or in combination on the basis of the technical common knowledge generally known to those skilled in the art.

In the present specification, the CD26 is preferably human CD26, and the anti-CD26 antibody is preferably an anti-human CD26 antibody. The anti-human CD26 monoclonal antibody of the present invention or the antigen-binding fragment thereof preferably binds to CD26 (preferably human CD26).

According to one embodiment, the anti-human CD26 monoclonal antibody of the present invention or the antigen-binding fragment thereof can be used in a set (i.e., in combination synchronously or metachronously) with an additional antibody, preferably an additional anti-CD26 antibody. Preferably, the anti-human CD26 monoclonal antibody of the present invention or the antigen-binding fragment thereof does not substantially exhibit competition for binding (does not have cross reactivity) with, for example, an anti-human CD26 antibody (preferably an anti-human CD26 humanized antibody, more preferably an anti-human CD26 humanized antibody YS110) serving as an antibody for treatment, or other anti-human CD26 antibodies (which may be, for example, anti-human CD26 monoclonal antibodies 4G8, 1F7, 5F8, 2F9, 16D4B, and 9C11 previously developed by the present inventors), i.e., noncompetitively binds to CD26. On the contrary, preferably, the anti-human CD26 monoclonal antibody of the present invention or the antigen-binding fragment thereof exhibits competition for binding (has cross reactivity) with these antibodies, i.e., competitively binds to CD26.

Whether two antibodies (one of which is the anti-human CD26 monoclonal antibody of the present invention or the antigen-binding fragment thereof, and the other of which may be an antibody to be compared) bind to the same epitope by respectively recognizing epitopes which are either identical or sterically overlapping can be determined by use of competitive assay. For example, the antigen CD26 is immobilized on a multi-well plate, and the blocking performance of an unlabeled antibody against the binding of a labeled antibody may be measured. General labeling for such competitive assay can be radioactive labeling or enzymatic labeling. In addition, the epitope to which the antibody binds can be determined by use of an epitope mapping technique well known to those skilled in the art.

The anti-human CD26 monoclonal antibody of the present invention or the antigen-binding fragment thereof can be purified or isolated according to a method generally known to those skilled in the art. Examples of the purification or isolation method include electrophoretic, molecular biological, immunological, and chromatographic approaches and specifically include ion-exchange chromatography, hydrophobic chromatography, reverse-phase HPLC chromatography, and isoelectric focusing electrophoresis.

The subject to which the anti-human CD26 monoclonal antibody of the present invention or the antigen-binding fragment thereof, or the composition for detecting human CD26 according to the present invention, comprising the anti-human CD26 monoclonal antibody or the antigen-binding fragment thereof is applied (e.g., contacted) is not limited and can be a mammal (a human or a nonhuman mammal (e.g., a mouse, a rat, a dog, a cat, a rabbit, cattle, a horse, sheep, a goat, or a pig)); or a non-mammalian animal (e.g., fish, a reptile, an amphibian, or a bird), a plant, an insect, a bacterium, or a (biological) sample derived therefrom (i.e., cells (including cultured cells), a tissue, an organ, a fragment thereof, or a material containing any of these samples). Alternatively, the subject may be an artificial environment (e.g., an in vitro reaction system). The subject according to the present invention is preferably a sample derived from a mammal, particularly, a human. According to one embodiment, preferably, such a sample contains, has contained, or is suspected of containing a tissue (e.g., tumor cells or immunocytes) expressing CD26.

The composition for detecting human CD26 according to the present invention is not particularly limited as long as the composition comprises the anti-human CD26 monoclonal antibody of the present invention or the antigen-binding fragment thereof and is capable of detecting CD26. In the present specification, the detection of (the expression of) CD26 may be the qualitative detection of CD26 or may mean the quantitative detection of CD26 (i.e., the measurement of the expression level of CD26).

According to one embodiment, desirably, the anti-human CD26 monoclonal antibody of the present invention or the antigen-binding fragment thereof is capable of detecting the overexpression of CD26. It should be understood that the overexpression of CD26 includes both of an increased expression level of CD26 compared with the typical expression level of CD26 in cells or tissues usually expressing CD26, and the expression of CD26 in tissues or cells usually expressing no CD26.

According to one embodiment, the anti-human CD26 monoclonal antibody of the present invention or the antigen-binding fragment thereof, or the composition for detecting human CD26, comprising the anti-human CD26 monoclonal antibody or the antigen-binding fragment thereof can be utilized in, for example:

the detection or analysis of the dynamics (distribution), expression, localization, etc., of CD26 in the subject;

the detection or analysis of change or abnormality in the expression level of CD26 (e.g., increase or decrease in the expression level of CD26 as compared with normal tissues as a control group);

the detection of information as an index for identifying a human CD26-related disease, or diagnosis based on this information;

the selection of a patient (preferably a human) suitable for the treatment of a human CD26-related disease using an anti-human CD26 antibody (preferably an anti-human CD26 humanized antibody, more preferably an anti-human CD26 humanized antibody YS110) serving as an antibody for treatment; or the monitoring of therapeutic effects (e.g., follow-up, confirmation of therapeutic efficacy, or evaluation of the expression of human CD26 in a patient (e.g. a case with relapse or a case nonresponsive to antibody therapy)) during or after the treatment of a human CD26-related disease using an anti-human CD26 antibody (preferably an anti-human CD26 humanized antibody, more preferably an anti-human CD26 humanized antibody YS110) serving as an antibody for treatment.

For example, when CD26 is highly expressed in a sample as compared with the expression level of CD26 in normal tissues as a control group, the subject (preferably human) from which this sample is derived can be determined and diagnosed as having a human CD26-related disease or having a high risk of developing a human CD26-related disease. For example, during or after the treatment of a patient having a human CD26-related disease using an antibody for treatment, a lesion site is collected as a subject to be treated, and change in the expression level of CD26 can be measured and observed to thereby determine the degree of progression or the degree of malignancy of the human CD26-related disease or use this change as an index for the efficacy of the treatment using the antibody for treatment.

The anti-human CD26 monoclonal antibody of the present invention or the antigen-binding fragment thereof, or the composition for detecting human CD26 according to the present invention, comprising the anti-human CD26 monoclonal antibody or the antigen-binding fragment thereof can be advantageously used as a clinical diagnostic agent or a marker of the stratification of a patient, which is required to produce a stable consequence about the policy or results of treatment targeting CD26.

In order to prepare the composition for detecting human CD26 according to the present invention, for example, a pharmacologically acceptable carrier, excipient, diluent, additive, disintegrant, binder, coating agent, lubricant, glidant, lubricating agent, solubilizing agent, solvent, gelling agent, antiseptic, and the like can be added, if necessary. Preferably, these additives do not inhibit the activity of the anti-human CD26 monoclonal antibody of the present invention or the antigen-binding fragment thereof and is nonreactive with the antigen CD26 as a subject to be detected. Standard additives known to those skilled in the art can be used without limitations, and the additives can be, for example, saline, tris-buffered saline, phosphate-buffered saline, a glucose solution of phosphate-buffered saline, water, or an albumin preparation or an emulsion such as an oil/water emulsion.

Also, the anti-human CD26 monoclonal antibody of the present invention or the antigen-binding fragment thereof can be used in a method for detecting human CD26 and, specifically, can be used in the detection of CD26, the analysis or monitoring of its expression level, the selection of a patient, etc., as mentioned above. The method for detecting human CD26 according to the present invention can comprise, for example, the steps of: contacting the anti-human CD26 monoclonal antibody of the present invention or the antigen-binding fragment thereof with a sample derived from a subject; and detecting human CD26, if present, in the sample by immunostaining.

The anti-human CD26 monoclonal antibody of the present invention or the antigen-binding fragment thereof may be contacted with a sample derived from a subject before administration or after the start of administration of an anti-human CD26 antibody (preferably an anti-human CD26 humanized antibody, more preferably an anti-human CD26 humanized antibody YS110) serving as an antibody for treatment of a human CD26-related disease, to thereby detect the expression of CD26. For example, for the purpose of administering the antibody for treatment a plurality of times, the dosing intervals and the number of doses of the antibody for treatment can be appropriately adjusted, and the expression of human CD26 in a sample derived from a subject of a patient having or suspected of having the human CD26-related disease may be detected once or more times during the treatment. When the epitope which is recognized (bound) by the anti-human CD26 monoclonal antibody of the present invention or the antigen-binding fragment thereof is different from an epitope which is recognized (bound) by the antibody for treatment, the anti-human CD26 monoclonal antibody or the antigen-binding fragment thereof does not exhibit competition for binding (does not cause cross reaction) with the antibody for treatment. Hence, the anti-human CD26 monoclonal antibody of the present invention or the antigen-binding fragment thereof is advantageous because CD26 can be accurately detected or evaluated using the anti-human CD26 monoclonal antibody or the antigen-binding fragment thereof even after the start of administration of the antibody for treatment.

Those skilled in the art can appropriately select and determine the necessary amount or concentration of the anti-human CD26 monoclonal antibody of the present invention or the antigen-binding fragment thereof, conditions for the preparation of the sample derived from a subject for detection, conditions for the contact between the sample and the antibody, detection conditions, etc., according to the purpose.

The anti-human CD26 monoclonal antibody of the present invention or the antigen-binding fragment thereof can also be used in a method for determining the suitability of administration of an antibody for treatment of a human CD26-related disease for a patient having or suspected of having the human CD26-related disease. The determination method can comprise, for example, the steps of: contacting the anti-human CD26 monoclonal antibody of the present invention or the antigen-binding fragment thereof with a sample derived from a subject; and detecting human CD26, if present, in the sample by immunostaining, and can further comprise, in some cases, the step of determining the suitability of administration of an antibody for treatment of a human CD26-related disease according to the degree of detection of human CD26 in the immunostaining. The term "according to the degree of detection of human CD26" is related to criteria of determination of the suitability of administration of an antibody for treatment, and those skilled in the art can arbitrarily set the criteria of determination according to the purpose. The criteria of determination may be set, for example, such that: when CD26 has been detected in the sample, the application of the antibody for treatment of a human CD26-related disease is regarded as positive; and when CD26 has not been detected, the application thereof is regarded as negative. The patient having or suspected of having the human CD26-related disease may preferably mean a human patient who currently has the human CD26-related disease, who has had this disease in the past, or who has the possibility of developing the human CD26-related disease now or in the future. The antibody for treatment of a human CD26-related disease can be an anti-human CD26 antibody and can be preferably an anti-human CD26 humanized antibody, more preferably an anti-human CD26 humanized antibody YS110.

In the present invention, the human CD26-related disease may refer to a disease or a condition related to the expression of CD26 and may be a disease or a condition related to the growth of cells expressing CD26. The human CD26-related disease is not limited and can be, for example, a cancer, an immune disease, a viral disease, a metabolic disease, or an inflammatory disease.

Examples of the cancer include, but are not limited to, benign tumors and primary or metastatic and invasive or noninvasive cancers, sarcomas, and mesotheliomas. The cancer can be, for example, malignant mesothelioma, liver cancer, kidney cancer, prostate cancer, colorectal cancer, lung cancer, thyroid gland cancer, T-cell malignant lymphoma, gastrointestinal stromal tumor (GIST), glioma, or any of other malignant tumors associated with the expression of CD26.

The immune disease can be, for example, autoimmune disease (e.g., rheumatoid arthritis, multiple sclerosis, or Basedow disease), graft versus host disease (GVHD), or any of other immune diseases associated with the expression of CD26. The autoimmune disease is not limited and may mean a disease or a condition resulting from the overreaction and attack of the immune system responsible for recognizing and eliminating foreign matter, against its own normal cells or tissues.

The viral disease can be, for example, disease caused by coronavirus.

The metabolic disease can be, for example, diabetes mellitus or metabolic syndrome.

The sample derived from a subject for use in the detection of CD26 using the anti-human CD26 monoclonal antibody of the present invention or the antigen-binding fragment thereof is preferably CD26-expressing cells, tissue, organ, a fragment thereof, or a material containing any of these samples, which has, has had, or has the possibility of having the aforementioned human CD26-related disease.

A method generally known to those skilled in the art can be used as a method for determining the binding affinity of the antibody or the antigen-binding fragment thereof for CD26. The binding affinity can be determined by use of, for example, Biacore® biosensor, KinExA biosensor, scintillation proximity assay, ELISA, ORIGEN immunoassay (IGEN Inc.), flow cytometry, fluorescence quenching, fluorescence transfer, yeast display, and/or immunostaining. The binding affinity may be screened by use of suitable bioassay. In order to select an anti-human CD26 monoclonal antibody or an antigen-binding fragment thereof having high CD26 binding affinity, candidates can be screened and narrowed down to one having a high amount of CD26 detected (high expression level of CD26) by using these methods alone or in combination.

According to one preferred embodiment, the anti-human CD26 monoclonal antibody of the present invention or the antigen-binding fragment thereof can be used for detecting CD26 (advantageously, human CD26) and is particularly preferably suitable for immunostaining.

According to one embodiment, the evaluation of the binding affinity for CD26 by flow cytometry can involve allowing the anti-human CD26 monoclonal antibody of the present invention or the antigen-binding fragment thereof in an unlabeled form to bind to a preparation as a subject to be evaluated (in this context, the preparation may refer to, for example, an individual, an organ, a tissue, cells, or a biological sample containing a fragment thereof or the like), followed by detection with a fluorescent dye-conjugated secondary antibody, or can involve directly labeling the anti-human CD26 monoclonal antibody of the present invention or the antigen-binding fragment thereof with a fluorescent dye (e.g., Alexa Fluor® 647), followed by detection.

According to one embodiment, the immunostaining of CD26 using the anti-human CD26 monoclonal antibody of the present invention or the antigen-binding fragment thereof is preferably performed for a fixed tissue preparation produced by fixing a preparation as a subject to be evaluated. The "fixing" may mean chemical treatment for protecting the preparation from autolysis or degradation caused by rotting. Such fixing is also expected to stop biochemical reaction and also improve physical strength or chemical stability in some cases.

The fixing can be performed in order to prevent the denaturation, degradation, or the like of the biological sample and maintain its form close to the natural state as much as possible, for the main purpose of research or testing. Preferably, the fixing inactivates endogenous biomolecules, particularly, proteolytic enzymes, in the biological sample; protects the biological sample from exogenous damages; in some cases, exhibits toxicity to microorganisms such as bacteria, or chemically modifies the biological sample into a form which resists being taken up as nutrients by microorganisms; and/or improves the strength or stability of the biological tissue itself.

Those skilled in the art can appropriately select the type (selection of a fixing agent, etc.) or conditions (the size of the preparation to be fixed, an approach of producing a section from the preparation, an approach of preventing the deformation of the preparation, the amount of the fixing agent, a fixing time, a container for use in the fixing, a fixing temperature, time, pH, etc.) of the fixing according to the purpose. As the approach of inactivating endogenous biomolecules in the biological sample, for example, these biomolecules may be denatured. Also, the biological sample in a gel or sol state may be rendered completely solid and thereby morphologically fixed for stabilization. Such fixing may employ physical denaturation based on temperature or pressure (e.g., boiling, heat coagulation by microwave irradiation, or freezing) and is preferably chemical treatment with a fixing agent. One or a combination of two or more fixing agents (fixatives) may be used and may be appropriately used in combination with a buffer for lessening pH variations, a salt or a sugar for adjusting osmotic pressure or viscosity, or the like.

Examples of the fixative include, but are not limited to, aldehyde fixatives, acid-containing fixatives, metal salt-containing fixatives, and dehydrator/organic solvent fixatives. The aldehyde fixatives are not limited, and a 10 to 25% formalin (saturated aqueous solution of formaldehyde) fixative can be used and may be supplemented, in some cases, with an additive, for example, sodium chloride, calcium chloride, sodium acetate, ammonium bromide, calcium chloride, or zinc sulfate. Alternatively, a 10% phosphate-buffered formalin fixative, a 4% paraformaldehyde fixative, or a 1 to 5% glutaraldehyde fixative, or the like may be used. Examples of the acid-containing fixatives include, but are not limited to, Bouin's fixatives (containing, for example, a saturated aqueous solution of picric acid:formalin:glacial acetic acid=15:5:1), Zamboni's fixatives, and fixatives containing a 2% osmium solution (using osmium tetroxide).

Examples of the metal salt-containing fixatives include, but are not limited to, zinc fixatives and Hollande fixatives. Examples of the dehydrator/organic solvent fixatives include, but are not limited to, alcohol (ethanol, etc.) fixatives, alcohol/formalin mixed solutions, FAA fixatives (containing, for example, formalin:glacial acetic acid:50% ethanol=1:1:18), and acetone fixatives. Preferred examples of the fixative include 10 to 25% formalin fixatives, 2 to 5% paraform fixatives, 80 to 100% ethanol, 80 to 100% methanol, and 100% acetone.

As for the size of the preparation to be fixed, a thin and small tissue slice is generally preferred because the fixing agent (fixative) is easily permeated thereinto. A preparation having a larger surface area is more preferred. According to one embodiment, the thickness of the preparation is 1.5 cm or smaller, more preferably 5 mm or smaller. The amount of the fixing agent is not particularly limited and can be a sufficient amount with respect to the preparation, for example, 5 times to 10 times the amount of the preparation. The fixing time may differ depending on the type of the fixing agent and the size and properties of the preparation. Insufficient fixing may result in tissue contraction or collapse of a fine structure, whereas excessive fixing may result in tissue contraction or swelling caused by the vulnerability of a tissue slice. Those skilled in the art can appropriately determine the optimum time for the fixing, which can be, for example, 6 hours to 48 hours. The fixing temperature can be, for example, 4° C. or room temperature. Although a higher temperature may shorten the fixing time, too high a temperature might harden the preparation.

Examples of approaches for the fixing include a dipping method which involves dipping a biological sample in a fixative as well as a perfusion method which involves injecting a sufficient amount of a fixative into the heart or the like to put the fixative onto a blood flow. The latter approach may be used in an in vivo pathological model experiment using, for example, mice.

The fixed biological sample can be preserved as a preparation, or can be further subjected to, for example, excision, dehydration, embedding, slicing, and/or staining, followed by, for example, observation under an optical microscope or the like.

The excision can decrease the preparation in size which permits microscopic observation when the preparation has a large size, or can be performed so as to facilitate the observation of lesion sites or normal sites in the preparation. The preparation can be appropriately cut.

In order to permit microscopic observation of the preparation or to prevent the deformation of the preparation by filling in hollow sites present in the preparation, the preparation can be embedded in an appropriate embedding agent (e.g., paraffin or celloidin) to thereby impart strength to the preparation. Examples of approaches for the embedding include, but are not limited to, a paraffin embedding method, a celloidin embedding method, an OCT compound embedding method, a gelatin embedding method, and a synthetic resin embedding method, all of which are generally known to those skilled in the art. According to one embodiment, the paraffin embedding method is preferred. If the preparation contains water when embedded, the embedding agent is not permeated into this portion. Hence, the water may be removed using an alcohol (ethanol, etc.).

In the case of using, for example, the paraffin embedding method, clearing using xylene or chloroform or the like is preferably performed for removing the alcohol permeated into the preparation in the dehydration process. Subsequently, paraffin is permeated into the preparation so that only paraffin is contained therein. Then, the preparation can be hardened by cooling to prepare a paraffin block.

In order to slice the preparation, a microtome may be used.

For facilitating the observation of the preparation under a microscope, it is preferred to stain the thus-obtained thin tissue section of the preparation (to visualize antigen-antibody reaction using an antibody which recognizes the antigen CD26) (those skilled in the art should understand that, hereinafter, the antibody for visualization may be an antigen-binding fragment in some cases).

In the case of preparing a paraffin block by use of, for example, the paraffin embedding method, the paraffin block can be deparaffinized using, for example, xylene or an alcohol (ethanol, etc.) and then, in some cases, can be strengthened for staining by the retrieval of the antigen of interest (CD26) in the preparation.

For example, the preparation thus fixed in formalin and embedded in paraffin may lose the immunogenicity of the antigen due to the occurrence of cross-linking which masks the antigen present in tissues or cells in the process of producing the preparation. This may inhibit antigen recognition by the antibody. Accordingly, in order to prevent such reduction in the immunogenicity, antigen retrieval treatment can be performed. Examples of methods for the antigen retrieval include, but are not particularly limited to: treatment with a proteolytic enzyme such as pepsin, trypsin, pronase, or protein kinase K; heat treatment by microwave, autoclaving, or boiling; and treatment with an alkali or an acid (e.g., hydrochloric acid or formic acid). Those skilled in the art can appropriately select and determine the retrieval method, the type, pH, and concentration of an antigen retrieval solution, a retrieval time, a retrieval temperature, etc., according to the purpose. In the case of, for example, the antigen retrieval by heat treatment, the heat treatment can be performed without limitations, for example, at 90° C. to 130° C. for 10 minutes to 1 hour using a citrate buffer solution of pH 6.0 to 7.0, a tris-HCl buffer solution of pH 9.0 to 11.0, a tris-EDTA buffer solution, an EDTA solution, urea, or any of various commercially available antigen retrieval solutions. In the case of the antigen retrieval by proteolytic enzyme treatment, those skilled in the art can appropriately determine the concentration of the proteolytic enzyme, and the enzyme treatment can be performed, for example, at 4° C. to 37° C. for approximately 5 minutes to several hours.

An enzyme labeled antibody method which involves labeling an antibody with a particular enzyme and then observing, under an optical microscope or the like, a color developed by a dye product formed through reaction with a substrate can be used as a method for visualizing antigen-antibody reaction (staining method). In the case of the observation under an optical microscope, for example, the contrast between a stained portion (signal portion) and an unstained portion (noise portion) (signal/noise ratio) can be visually observed. Alternatively, a virtual slide may be prepared and used in the quantitative analysis of a staining site to thereby evaluate the stained portion.

General examples of the enzyme labeled antibody method include a direct method which performs the antigen-antibody reaction once by labeling with an antibody (primary antibody) reacting directly with an antigen, and an indirect method which performs the antigen-antibody reaction two or more times (mostly two times, and in some cases, 3 times) by performing the first antigen-antibody reaction using an unlabeled primary antibody, which is then reacted with a different labeled antibody (secondary antibody), which targets the primary antibody itself as an antigen. For example, a PAP method using a peroxidase/anti-peroxidase antibody soluble immunocomplex (PAP) (Sternberger L A et al. (1970). "The unlabeled antibody enzyme method of immunohistochemistry: preparation and properties of soluble antigen-antibody complex (horseradish peroxidase-antihorseradish peroxidase) and its use in identification of spirochetes". J Histochem Cytochem 18 (5): 315-33. PMID 4192899.), a LAB (linked avidin-biotin) method, an ABC method using an avidin/biotin complex (Hsu S M, Raine L, Fanger H (1981). "Use of avidin-biotin-peroxidase complex (ABC) in immunoperoxidase techniques: a comparison between ABC and unlabeled antibody (PAP) procedures". J Histochem Cytochem 29 (4): 577-80.), a LSAB (linked streptavidin-biotin) method using streptavidin, a TSA (tyramide signal amplification) method, or a CARD (catalyzed reporter deposition) method may be used as a modified version of the indirect method.

Examples of color development methods for the enzyme labeled antibody method may include, but are not limited to: a DAB method (brown staining) which involves reacting peroxidase (horseradish peroxidase, etc.) as a labeling enzyme with a chromogenic substrate diaminobenzidine (DAB) (Graham R C Jr, Karnovsky M J. (1966). "The early stages of absorption of injected horseradish peroxidase in the proximal tubules of mouse kidney: ultrastructural cytochemistry by a new technique". J Histochem Cytochem (4): 291-302); a more highly sensitive nickel DAB method which involves performing the DAB method in the presence of nickel ions; a method (red staining) which involves reacting peroxidase with a chromogenic substrate aminoethylcarbazole (AEC); a method (blue-purple staining) which involves reacting alkaline phosphatase as a labeling enzyme with a chromogenic substrate BCIP/NBT; a method (red staining) which involves reacting alkaline phosphatase as a labeling enzyme with a chromogenic substrate Fast Red; and a method (blue staining) which involves reacting alkaline phosphatase as a labeling enzyme with a chromogenic substrate Fast Blue.

According to one embodiment, when the staining method is the DAB method, the antigen-retrieved preparation is preferably dipped in, for example, methanol containing hydrogen peroxide water, before staining to thereby inactivate endogenous peroxidase in the preparation.

Those skilled in the art can appropriately select and determine various conditions such as a staining approach, a staining temperature, and a staining time according to the purpose. For the staining, for example, the anti-human CD26 monoclonal antibody of the present invention or the antigen-binding fragment thereof may be added as a primary antibody to the preparation and reacted therewith, for example, at 4° C. to room temperature for 1 hour to overnight, followed by the washing of the primary antibody. Subsequently, a peroxidase-labeled antibody or an alkaline phosphatase-labeled antibody can be added as a secondary antibody to the preparation and reacted therewith, for example, at 4° C. to room temperature for 30 minutes to overnight, followed by the washing of the secondary antibody and subsequent color development. Alternatively, in order to enhance the detection sensitivity, the ABC method may be used. Alternatively, in order to enhance the detection sensitivity, the first antigen-antibody reaction may be performed using an unlabeled primary antibody (the anti-human CD26 monoclonal antibody of the present invention or the antigen-binding fragment thereof), then the second antigen-antibody reaction can be performed using an unlabeled secondary antibody which targets the primary antibody itself as an antigen, and subsequently a peroxidase- or alkaline phosphatase-labeled tertiary antibody which targets the secondary antibody itself as an antigen can be added to the preparation and reacted therewith, for example, at 4° C. to room temperature for 1 hour to overnight, followed by the washing of the tertiary antibody and subsequent color development.

In addition to the aforementioned antigen-antibody reaction, an autoradiography method which involves conjugating (or "labeling") an antibody with a radioisotope and then exposing printing paper thereto; a gold colloid method which involves conjugating an antibody with a visible material such as gold particles, followed by observation under an electron microscope or the like; or a fluorescent antibody method which involves labeling an antibody with a fluorescent dye, and irradiating the labeled antibody with an excitation wavelength after antigen-antibody reaction to develop fluorescence, which is then observed under a fluorescence microscope may be used as the method for visualizing antigen-antibody reaction.

In an alternative aspect, the present invention relates to a hybridoma (i.e., clone 19 (Accession No. MITE BP-01642), clone 18 (Accession No. NITE BP-01643), or clone 16 (Accession No. NITE BP-01644), which is a hybridoma deposited with the Patent Microorganisms Depositary of the National Institute of Technology and Evaluation (NITE); deposition date: Jul. 3, 2013 for all of these hybridomas). These hybridomas include progeny resulting from cell division, and the progeny is not necessarily required to be identical to the parent cells due to mutation or the like.

In an alternative aspect, the present invention also provides a DNA (polynucleotide) encoding the anti-human CD26 monoclonal antibody or the antigen-binding fragment thereof, a vector containing the DNA, and a host cell containing the vector. Their production methods, their obtainment methods, and the type of the vector or the host cell are well known to those skilled in the art.

The hybridoma, the anti-human CD26 monoclonal antibody, the antigen-binding fragment thereof, the DNA (polynucleotide) encoding the anti-human CD26 monoclonal antibody or the antigen-binding fragment thereof, the vector containing the DNA, or the host cell containing the vector according to the present invention may be in an isolated form, i.e., a non-naturally occurring form, and may be artificially purified. According to one embodiment, preferably, these are substantially pure without containing other impurities.

Those skilled in the art should understand that the present invention may be carried out by any one of or appropriate combination of two or more of all aspects described in the present specification unless a technical contradiction arises. Further, those skilled in the art should understood that the present invention can be preferably carried out by an appropriate combination of all preferable or advantageous aspects described in the present specification unless a technical contradiction arises.

Literatures cited in the present specification should be interpreted as being incorporated herein by reference in their entirety. Those skilled in the art can understand related contents disclosed in these literatures by reference as a part of the present specification without departing from the spirits and scope of the present invention according to the context of the present specification.

Literatures cited in the present specification are provided merely for the purpose of disclosing related techniques before the filing date of the present application. It should not be understood that the present inventors admit to having no right preceding such disclosure due to the prior inventions or any other reasons. All statements of these literatures are based on information which has been available by the present applicant, and there is no admission that the contents of these statements are accurate.

The terms in the present specification are used for illustrating particular embodiments and are not intended to limit the invention.

The term "comprising" used in the present specification means that described items (members, steps, factors, numbers, etc.) are present and the presence of the other items (members, steps, factors, numbers, etc.) is not excluded therefrom, unless the context evidently requires different interpretation. The term "comprising" encompasses aspects described by the terms "consisting of" and/or "consisting essentially of".

All terms (including technical terms and scientific terms) used herein have the same meanings as those understood in a broad sense by those skilled in the art to which the present invention belongs, unless otherwise defined. The terms used herein should be interpreted as having meanings consistent with meanings in the present specification and related technical fields and should not be interpreted in an idealized or excessively formal sense, unless otherwise defined.

The embodiments of the present invention may be described with reference to a schematic diagram. However, such a schematic diagram may be exaggerated for the purpose of clear illustration.

Terms such as "first" or "second" are used for expressing various factors. However, these factors are understood to be not limited by these terms. These terms are used merely for differentiating one factor from the other factors. For example, the first factor may be described as the second factor, and vice versa, without departing from the scope of the present invention.

In the present specification, it should be understood that numerical values used for indicating component contents, numerical ranges, etc., are modified with the term "approximately" unless otherwise specified. For example, "4° C." is interpreted as meaning "approximately 4° C." unless otherwise specified. Those skilled in the art can naturally understand the extent thereof rationally according to the technical common knowledge and the context of the present specification.

It should be understood that each aspect indicated in a singular form used in the present specification and claims may be in a plural form, and vice versa, unless the context evidently requires different interpretation and unless a technical contradiction arises.

Hereinafter, the present invention will be described in more detail with reference to Examples. However, the present invention can be embodied by various aspects and is not intended to be limited by Examples described herein. Those skilled in the art can implement the present invention by various changes or modifications, additions, deletions, substitutions, etc., without departing from the spirit or scope of the present invention.

EXAMPLES

1. Study Method (1) Anti-Human CD26 Antibody Used in Study

The anti-human CD26 antibodies used were mouse anti-human CD26 monoclonal antibodies previously developed by the present inventors:

(i) 4G8 binding to amino acids 1 to 247 of human CD26,
(ii) 1F7 binding to amino acids 248 to 358 of human CD26, and an anti-human CD26 humanized antibody YS110 prepared on the basis of the complementarity-determining regions of 14D10 binding to the same site thereas,
(iii) 5F8 and 2F9 binding to the neighborhood of amino acid 358 of human CD26,
(iv) 16D4B binding to amino acids 450 to 577 of human CD26, and
(v) 9C11 binding to amino acids 359 to 653 of human CD26. YS110 is available from Y's Therapeutics Co., Ltd. (Tokyo, Japan).

For 4G8, 14D10, 2F9, 16D4B, and 9C11, see, for example, "Dong R P, Tachibana K, Hegen M, et al. (1998) Correlation of the epitopes defined by anti-CD26 mAbs and CD26 function. Mol Immunol 35: 13-21".

For 1F7, see, for example, "Morimoto C, et al. (1989) 1F7, A novel cell surface molecule, involved in helper function of CD4 cells. J Immunol 143: 3430-3439" and WO 2002/092127.

For 5F8, see, for example, "Torimoto Y et al. (1992) Biochemical characterization of CD26 (dipeptidyl peptidase IV): Functional comparison of distinct epitopes recognized by various anti-CD26 monoclonal antibodies. Molecular Immunology Vol. 29, No. 2, 183-192" and WO 2002/092127.

For 14D10, see, for example, WO 2007/014169.

The anti-human CD26 humanized antibody YS110 is an antibody which is specified by Accession No. PTA-7695 of American Type Culture Collection (ATCC) and produced by a line designated as s604069.YST-pABMC148 (x411). For the details thereof, see, for example, Patent Literature 1.

Monoclonal antibody clone 44-4 (catalog No. D068-1) commercially available from MBL (Medical & Biological Laboratories Co., Ltd.) as a mouse anti-human CD26 monoclonal antibody capable of immunohistological staining, and a goat anti-human CD26 polyclonal antibody (catalog No. AF1180) from R&D Systems, Inc. were used as controls to be compared with the anti-human CD26 monoclonal antibody of the present invention newly established in this study.

(2) Preparation of Immunizing Antigen (Human CD26 Protein)

A CHO cell line was transfected with a plasmid for the expression of soluble human CD26 (human CD26 (SEQ ID NO: 1) from which its N-terminal amino acid residues 3 to 9 had been deleted) prepared by the present inventors to clone a CHO cell line stably secreting human CD26 (Tanaka T, Duke-Cohan J S, Kameoka J, et al. (1994) Enhancement of antigen-induced T-cell proliferation by soluble CD26/dipeptidyl peptidase IV. Proc Natl Acad Sci USA 91: 3082-3086). A culture supernatant containing the secreted soluble human CD26 was passed through an adenosine deaminase (ADA)-immobilized Sepharose column for the affinity purification of the soluble human CD26 (idem). The purified soluble human CD26 was mildly stirred in a urea buffer (8 M urea, 20 mM HEPES, and 50 mM DTT) at room temperature for 5 to 8 hours to prepare denatured human CD26.

(3) Immunization of Mouse and Preparation of Hybridoma

After replacement of the solvent for the denatured soluble human CD26 with phosphate-buffered saline (PBS), the concentration of the antigen was adjusted to 100 μg/50 μl. The antigen solution was mixed with 50 μl of a synthetic copolymer adjuvant TiterMax Gold (TiterMax USA Inc.), and the mixture was subcutaneously injected at 100 μl/dose to each BALB/c mouse. A total of 7 shots of subcutaneous injection were performed at 2-week intervals. Finally, 50 μl, which was half of the above amount, was intravenously injected to the tail vein of the mouse. Three days later, partially purified splenocytes obtained by the dissection of the mouse were mixed with P3U1 myeloma cells at a ratio of 1:1, and these cells were fused using polyethylene glycol to prepare hybridomas. After washing of the cells, the cells were suspended in an RPMI1640 medium containing 10% FCS (fetal calf serum), 5% BriClone (NICB catalog No. BRBR001), and HAT (hypoxanthine, aminopterin, and thymidine) (Invitrogen Corp.) and then seeded to a 96-well flat-bottomed plate. The culture supernatants of grown hybridomas were recovered and screened for anti-human CD26 antibody-producing hybridomas by flow cytometry and ELISA to select positive hybridomas, followed by the study of immunostaining. Hybridomas capable of immunostaining were reseeded at one cell/well to a 96-well flat-bottomed plate to select a plurality of single clones. After replacement of the medium for use in culture with a serum-free GIT medium (Wako Pure Chemical Industries, Ltd.), an IgG fraction was purified from each cell culture supernatant containing the antibody of interest using Protein A IgG Purification Kit (Pierce/Thermo Fisher Scientific Inc.).

(4) Flow Cytometry

A human CD26-integrated Jurkat cell line (Jurkat-CD26WT) prepared by the present inventors (Tanaka T, Kameoka J, Yaron A, Schlossman S F, Morimoto C (1993) The costimulatory activity of the CD26 antigen requires dipeptidyl peptidase IV enzymatic activity. Proceedings of the National Academy of Sciences of the United States of America 90: 4586-4590) was used to study binding to human CD26. A primary antibody solution of the hybridoma culture supernatant or anti-human CD26 monoclonal antibody clone 44-4 from MBL (Medical & Biological Laboratories Co., Ltd.) was added at 100 µl/sample to the cells, or a primary antibody solution of mouse anti-human CD26 monoclonal antibody clone 5F8 diluted to 20 µg/ml was added at 50 µl/sample to the cells, and the mixture was left standing at 4° C. for 25 minutes. Then, the cells were washed with ice-cold PBS. A solution of a PE-labeled goat anti-mouse IgG antibody (BD Biosciences) as a secondary antibody diluted to 400 ng/ml was added thereto at 50 µl/sample, and the mixture was left standing at 4° C. for 25 minutes. The cells were washed with ice-cold PBS and then assayed using a flow cytometer FACSCalibur (BD Biosciences). The obtained data was analyzed using FlowJo (Tree Star Inc.).

(5) Enzyme-Linked Immunosorbent Assay (ELISA)

The purified soluble human CD26 (undenatured human CD26) or the soluble human CD26 treated with a urea buffer (denatured human CD26) was diluted to 4 µg/ml with a carbonate/bicarbonate buffer (CBB) and added at 50 µl/well to Immunoplate (NUNC), and the mixture was left standing overnight at 4° C. A group supplemented with only a CBB buffer without being coated with the soluble human CD26 was prepared as a negative control. After washing with a phosphate-buffered saline containing 0.05% Tween 20 (PBS-T), PBS-T containing 3% BSA (bovine serum albumin) was added thereto at 100 µl/well, and the mixture was left standing at room temperature for 1 hour to block the plate. After washing with PBS-T, a primary antibody solution of the hybridoma culture supernatant diluted 3-fold with PBS-T, an anti-human CD26 monoclonal antibody clone 44-4 from MBL (Medical & Biological Laboratories Co., Ltd.) was added thereto at 50 µl/well, or a primary antibody solution of a goat anti-human CD26 polyclonal antibody from R&D Systems, Inc. or mouse anti-human CD26 monoclonal antibody clone 5F8 diluted to 1 µg/ml with PBS-T was added thereto at 50 µl/well, and the mixture was left standing at room temperature for 1 hour. After washing with PBS-T, a secondary antibody solution of an HRP-conjugated goat anti-mouse IgG antibody (BD Biosciences) diluted 500-fold with PBS-T (no concentration is described in the product) or an HRP-conjugated donkey anti-goat IgG antibody (Santa Cruz Biotechnology, Inc.) diluted to 160 ng/ml was added thereto at 50 µl/well, and the mixture was left standing at room temperature for 1 hour. After washing with PBS-T, TMB peroxidase substrate (KPL, Kirkegaard & Perry Laboratories, Inc.) was added thereto at 50 µl/well, and the reaction was terminated by the addition of 2 N $H_2SO_4$ at 25 µl/well. Then, the absorption wavelength at 450 nm and the reference wavelength at 570 nm were measured using a microplate reader (Bio-Rad Laboratories, Inc.).

(6) Immunohistological Staining

Each 5-µm thick preparation was prepared from a section fixed in a 10 to 25% formalin fixative or alcohol fixative or the like and embedded in paraffin, and then deparaffinized, followed by retrieval. The retrieval method was performed by (1) autoclaving at 120° C. for 20 minutes in a 10 mM citrate buffer solution of pH 6.0, (2) boiling at 100° C. for 10 minutes in a 10 mM citrate buffer solution of pH 6.0, (3) treatment with 0.01 to 0.1% trypsin at room temperature or 37° C. for 5 to 60 minutes, or (4) treatment with 0.01 to 0.04% protein kinase K at room temperature or 37° C. for 5 to 30 minutes.

The results of FIGS. 2A and 2B were obtained by the retrieval method (1).

Then, the retrieved preparation was dipped in methanol containing hydrogen peroxide water to inactivate endogenous peroxidase, followed by blocking with 2.5% horse serum. Then, a primary antibody solution of the culture supernatant of each hybridoma or anti-human CD26 monoclonal antibody clone 44-4 from MBL (Medical & Biological Laboratories Co., Ltd.) was added at 100 µl/sample to the preparation, or a primary antibody solution of an IgG antibody purified from the culture supernatant of each hybridoma or a goat anti-human CD26 polyclonal antibody from R&D Systems, Inc. diluted to 10 µg/ml with PBS containing 0.2% BSA was added at 100 µl/sample to the preparation, and reacted therewith at 4° C. or room temperature for 1 hour to overnight. After washing, an HRP-conjugated horse anti-mouse IgG antibody or an HRP-conjugated horse anti-goat IgG antibody (Vector Laboratories Ltd.) was added as a secondary antibody at 100 µl/sample to the preparation and reacted therewith at 4° C. or room temperature for 30 minutes to overnight. After further washing, a color was developed with DAB (diaminobenzidine) (Dojindo Laboratories) and hydrogen peroxide and observed under Axio Scope. Al optical microscope (Carl Zeiss A G).

The results of staining human CD26 were evaluated by two pathologists by comparing each of the human CD26 staining patterns of human normal tissues (liver, kidney, and prostate tissues) and human cancer tissues (malignant mesothelioma, hepatocellular carcinoma, renal cell carcinoma, prostate cancer, colon adenocarcinoma, and lung adenocarcinoma) expressing human CD26 with the case of staining with the goat anti-human CD26 polyclonal antibody from R&D Systems, Inc.

(7) Analysis of Competition with Anti-Human CD26 Humanized Antibody and Existing Anti-Human CD26 Monoclonal Antibody A plurality of anti-human CD26 monoclonal antibodies of the present invention obtained were each analyzed for the competition with an anti-human CD26 humanized antibody YS110 using Jurkat-CD26WT by flow cytometry. Specifically, a solution of the anti-human CD26 humanized antibody YS110 or a control human IgG antibody (Kenketsu Venilon®-I, Chemo-Sero-Therapeutic Research Institute (Kaketsuken)) diluted to 50 µg/ml was added at 50 µl/sample to Jurkat-CD26WT, and the mixture was left standing at 4° C. for 30 minutes. Then, the cells were washed with ice-cold PBS. The aforementioned hybridoma culture supernatant was added thereto at 100 µl/sample, and the mixture was left standing at 4° C. for 25 minutes. After washing of the cells with ice-cold PBS, a solution of a PE-labeled goat anti-mouse IgG antibody as a secondary antibody diluted to 400 ng/ml was added thereto at 50 µl/sample, and the mixture was left standing at 4° C. for 25 minutes. The cells were washed with ice-cold PBS and then assayed using FACSCalibur (BD Biosciences).

Similarly, 5 types of existing monoclonal antibodies differing in epitope from each other (4G8, 1F7, 5F8, 16D4B, and 9C11) and an anti-human CD26 monoclonal antibody produced by clone 18 or clone 19 mentioned later in "2 Results" described below were analyzed for competition for binding by flow cytometry (see "Dong R P, Tachibana K, Hegen M, et al. (1998) Correlation of the epitopes defined by anti-CD26 mAbs and CD26 function. Mol Immunol 35: 13-21"). Specifically, a solution of each of these 5 types of anti-CD26 monoclonal antibodies or a control mouse $IgG_1$ antibody (BioLegend, Inc., clone MG1-45, catalog No. 401404) diluted to 50 µg/ml was added at 50 µl/sample to Jurkat-CD26WT, and the mixture was left standing at 4° C. for 30 minutes. Then, the cells were washed with ice-cold PBS. The purified IgG antibody (derived from the culture supernatant of clone 18 or clone 19) labeled directly with Alexa Fluor® 647 using Alexa Fluor® 647 Monoclonal Antibody Labeling Kit (Molecular Probes, catalog No. A-20186) was added thereto at 0.6 µg/ml and 50 µl/sample, and the mixture was left standing at 4° C. for 25 minutes. Then, the cells were washed with ice-cold PBS and assayed using FACSCalibur (BD Biosciences).

(8) Epitope Mapping

Full-length human CD26 and 5 types of human CD26-deletion mutants were prepared, and COS-7 cells were transfected with each of their plasmids to express the full-length human CD26 protein and the 5 types of human CD26 mutated proteins. The 5 types of human CD26-deletion mutants relate to a deletion mutant consisting of amino acid residues 1 to 247 of the full-length human CD26 (amino acid residues 1 to 766), a deletion mutant consisting of amino acid residues 1 to 358 thereof, a deletion mutant consisting of amino acid residues 1 to 449 thereof, a deletion mutant consisting of amino acid residues 1 to 577 thereof, and a deletion mutant consisting of amino acid residues 1 to 739, respectively (see "Dong R P, Tachibana K, Hegen M, et al. (1998) Correlation of the epitopes defined by anti-CD26 mAbs and CD26 function. Mol Immunol 35: 13-21"). The anti-human CD26 humanized antibody YS110 or the purified IgG antibody (derived from the culture supernatant of clone 18 or clone 19) labeled directly with Alexa Fluor® 647 was added at 0.6 µg/ml and 50 µl/sample to the COS-7 cells for each of these proteins, and the mixture was left standing at 4° C. for 25 minutes. Then, the cells were washed with ice-cold PBS and analyzed for the binding of each antibody to the full-length human CD26 or each human CD26-deletion mutant using FACSCalibur (BD Biosciences).

2. Results (1) Screening of Hybridoma Culture Supernatant

As mentioned above, partially purified splenocytes of the mouse immunized with the soluble human CD26 treated by denaturation with a urea buffer were fused with P3U1 myeloma cells, and hybridoma culture supernatants containing the mouse anti-human CD26 monoclonal antibody were recovered from grown hybridomas and narrowed down to hybridomas producing the anti-human CD26 monoclonal antibody by primary screening based on flow cytometry and secondary screening based on ELISA. As a result, 31 hybridoma clones capable of detecting human CD26 were obtained by flow cytometry and ELISA. The results of flow cytometry of typical clones are shown in FIG. 1A, and the results of ELISA for the undenatured soluble human CD26 and the urea buffer-denatured soluble human CD26 are shown in FIG. 1B.

(2) Immunostaining with Hybridoma Culture Supernatant and Purified IgG Antibody

The culture supernatants of the 31 hybridoma clones thus obtained by screening were used to study the immunostaining of human CD26.

First, an attempt was made to stain the antigen with anti-human CD26 monoclonal antibody clone 44-4 from MBL (Medical & Biological Laboratories Co., Ltd.) according to the method described in the product document of MBL (Medical & Biological Laboratories Co., Ltd.) (http://ruo.mbl.co.jp/dtl/A/D068-1/). The anti-human CD26 monoclonal antibody clone 44-4, however, was found poorly reliable because of its weak staining properties and scarce staining, and thus unsuitable as a (companion) diagnostic agent for selecting a patient applicable to human CD26 antibody therapy (FIG. 2A). Even Western blotting using the anti-human CD26 monoclonal antibody clone 44-4 from MBL (Medical & Biological Laboratories Co., Ltd.) failed to detect human CD26 (data not shown).

Next, the culture supernatants of the 31 hybridoma clones producing the anti-human CD26 monoclonal antibody which can be used in flow cytometry and ELISA, prepared by the present inventors, were used to study the immunostaining of human normal tissues (liver, kidney, and prostate tissues) and malignant mesothelioma. As a result, as with the polyclonal antibody from R&D Systems, Inc., 6 clones confirmed to stain human CD26 in the bile canaliculi of the liver, the brush border of the proximal convoluted tubule, the luminal side of the prostate, etc., were obtained. The results of immunohistological staining using typical 3 clones (clone 16, clone 18, and clone 19) among these clones and 1 clone (clone 3) as a negative control example are shown in FIG. 2A. All of the culture supernatants containing the anti-human CD26 monoclonal antibodies produced by clone 16, clone 18, and clone 19, respectively, exhibited high human CD26 staining intensity (human CD26 was stained brown) and low background in any of the human normal tissues (liver, kidney, and prostate tissues) and the malignant mesothelioma tissue, as compared with anti-human CD26 monoclonal antibody clone 44-4 from MBL (Medical & Biological Laboratories Co., Ltd.).

Each IgG fraction (IgG antibody) obtained by the purification of the hybridoma culture supernatant of clone 18 or clone 19 was further used to study the immunostaining of human CD26-positive tumors (hepatocellular carcinoma, renal cell carcinoma, prostate cancer, colon adenocarcinoma, and lung adenocarcinoma). As a result, the purified antibodies derived from clone 18 and clone 19, respectively, were confirmed to exhibit distinct staining equivalent to the polyclonal antibody from R&D Systems, Inc. for any of the cancer tissues (FIG. 2B).

The hybridoma clone 19, clone 18, and clone 16 were each deposited with the Patent Microorganisms Depositary of the National Institute of Technology and Evaluation (NITE) (2-5-8, Kazusakamatari, Kisarazu, Chiba, 292-0818, Japan) (deposition date: Jul. 3, 2013 for all of these hybridomas) under Accession No. NITE BP-01642 for clone 19, Accession No. NITE BP-01643 for clone 18, and Accession No. NITE BP-01644 for clone 16.

(3) Analysis of Competition with Anti-Human CD26 Humanized Antibody

The culture supernatants of the hybridoma clone 16, clone 18, and clone 19 were used to analyze, by flow cytometry, the competition with the anti-human CD26 humanized antibody YS110 under clinical trial. As a result, when human CD26 was pretreated with the anti-human CD26 humanized antibody YS110, the binding to human CD26 of the anti-human CD26 monoclonal antibody contained in the culture supernatant of clone 16 or clone 19 was not inhibited at all (i.e., the monoclonal antibody did not exhibit competition for binding with YS110), whereas when human CD26 was pretreated with YS110, the binding to human CD26 of the anti-human CD26 monoclonal antibody contained in the culture supernatant of clone 18 was completely inhibited (FIG. 3). The results of analyzing each clone by flow cytometry are shown in FIG. 6. These results demonstrated that the anti-human CD26 monoclonal antibody produced by clone 19, which exhibited particularly distinct staining properties, among the 3 clones obtained can recognize human CD26 without the inhibition of its binding by the anti-human CD26 humanized antibody YS110. This clone would be particularly useful in the clinical examination of a sample from a patient given the anti-human CD26 humanized antibody YS110.

(4) Epitope Mapping

In order to further secure the results about the competition with the anti-human CD26 humanized antibody YS110, typical 2 clones (clone 18 and clone 19) which produced distinct staining results were used to identify their respective epitopes.

As a result, the binding to human CD26 of the anti-human CD26 monoclonal antibody produced by clone 18 was completely inhibited by the anti-CD26 monoclonal antibody 1F7 binding to amino acid residues 248 to 358 of the full-length human CD26 protein. On the other hand, the binding to human CD26 of the anti-human CD26 monoclonal antibody produced by clone 19 was shown to be completely inhibited by the anti-human CD26 monoclonal antibody 4G8 binding to amino acid residues 1 to 247 of the full-length human CD26 protein (FIG. 4).

In addition, full-length human CD26 and 5 types of human CD26-deletion mutated proteins were each expressed in COS-7 cells, and analyzed by flow cytometry for the binding to each of these proteins of the anti-human CD26 monoclonal antibody produced by clone 18 or clone 19. The anti-human CD26 monoclonal antibody produced by clone 18 bound to amino acid residues 1 to 358 of human CD26, but did not bind to amino acid residues 1 to 247 thereof, demonstrating that this antibody binds to an epitope on amino acid residues 248 to 358 of human CD26 (FIGS. 5 and 8). On the other hand, the anti-human CD26 monoclonal antibody produced by clone 19 bound to all of the full-length CD26 and the 5 types of CD26-deletion mutated proteins, demonstrating that this antibody binds to an epitope on amino acid residues 1 to 247 of human CD26 (FIGS. 5 and 8).

These results were completely consistent with the results of analyzing the competition with the anti-human CD26 humanized antibody YS110 (FIG. 4), and also in agreement with the results showing that the binding of the anti-human CD26 monoclonal antibody produced by clone 18 was completely inhibited by the anti-human CD26 humanized antibody YS110 binding to amino acids 248 to 358 of human CD26 while the binding of the antibody from clone 19 was not inhibited by YS110 (FIGS. 3 and 6).

As a result of also analyzing clone 16 for the competition with the anti-human CD26 humanized antibody YS110, the anti-human CD26 monoclonal antibody produced by clone 16 was shown to almost completely inhibit the binding to human CD26 of the anti-CD26 monoclonal antibody (16D4B) binding to amino acid residues 450 to 577 of human CD26, and further shown to completely inhibit the binding to human CD26 of the anti-human CD26 monoclonal antibody (9C11) binding to amino acid residues 359 to 653 of human CD26 (FIG. 7), demonstrating that this antibody binds to an epitope on amino acid residues 359 to 653. These results were also in agreement with the results showing that the binding of the anti-human CD26 monoclonal antibody produced by clone 16 was not inhibited by the anti-human CD26 humanized antibody YS110 (FIGS. 3 and 6).

3. Discussion

The conventional anti-human CD26 monoclonal antibody failed to achieve the immunostaining of the fixed tissue preparation. Although only anti-human CD26 polyclonal antibodies from R&D Systems, Inc. and Novus Biologicals, LLC can be used in immunostaining (http://www.rndsystems.com/Products/AF1180; http://www.novusbio.com/CD26-Antibody_NB100-59021.html), the antibody from R&D Systems, Inc. is an antibody affinity-purified with soluble human CD26 and therefore regarded as better than the antibody from Novus Biologicals, LLC. Since these anti-human CD26 antibodies, however, are polyclonal antibodies, the major problem thereof is lot-to-lot variations. These antibodies may be acceptable as research reagents, but are unsuitable as clinical diagnostic agents or markers of the stratification of a patient, which are required to produce a stable consequence about the policy or results of treatment targeting CD26.

Anti-human CD26 monoclonal antibody clone 44-4 is sold for research from MBL (Medical & Biological Laboratories Co., Ltd.) (http://ruo.mbl.co.jp/dtl/A/D068-1/), but is unsuitable as a clinical diagnostic agent, which is inevitably required to produce a stable consequence, because of its very weak staining properties and scarce staining in the immunostaining of the fixed tissue preparation (FIG. 2).

This time, the present inventors identified a novel anti-human CD26 monoclonal antibody which is suitable for the immunostaining of various human CD26-positive tumors and can be used as a companion diagnostic agent exhibiting a staining pattern equivalent to the affinity-purified polyclonal antibody from R&D Systems, Inc.

First, each mouse was immunized with recombinant soluble human CD26 denatured with a urea buffer, and then used to prepare hybridomas. As a result, the anti-human CD26 monoclonal antibody clone 44-4 from MBL (Medical & Biological Laboratories Co., Ltd.) (http://ruo.mbl.co.jp/dtl/A/D068-1/) exhibited very weak staining, whereas a novel anti-human CD26 monoclonal antibody which exerted staining properties equivalent to the polyclonal antibody from R&D Systems, Inc. was successfully obtained.

As a result of epitope mapping of typical 3 clones capable of immunostaining, their epitopes were found very diverse.

The anti-human CD26 monoclonal antibody produced by clone 16 or clone 19 was shown to have an epitope different from that of the anti-human CD26 humanized antibody YS110. These antibodies, which can be used in flow cytometry, ELISA, and immunostaining without competing with the anti-human CD26 humanized antibody YS110, are particularly preferred as (companion) diagnostic agents, for example, for selecting a patient applicable to anti-human CD26 humanized antibody therapy using YS110 or for monitoring therapeutic effects (e.g., follow-up or evaluation of the expression of human CD26 in a case with relapse or a case nonresponsive to antibody therapy) after the anti-human CD26 humanized antibody therapy. These antibodies can also be utilized in research on CD26 in order to analyze (e.g., follow-up) the expression of CD26 in tumors or human immunocytes after administration of YS110. For example, if an antibody whose binding is inhibited by YS110 is used for following-up the expression of CD26 in T-cells or tumors by flow cytometry or immunostaining after administration of YS110 in an in vivo pathological model experiment using mice or the like, CD26 cannot be accurately detected or evaluated even if CD26 is expressed in these T-cells or tumors. Hence, these antibodies are also useful for the progression of research on CD26.

INDUSTRIAL APPLICABILITY

The anti-human CD26 monoclonal antibody of the present invention or the antigen-binding fragment thereof can be advantageously utilized in the medical field and the research field of CD26.

The invention claimed is:

1. An anti-human CD26 monoclonal antibody or an antigen-binding fragment thereof, produced by
    a hybridoma deposited under Accession No. NITE BP-01642,
    a hybridoma deposited under Accession No. NITE BP-01643, or
    a hybridoma deposited under Accession No. NITE BP-01644.

2. The anti-human CD26 monoclonal antibody or the antigen-binding fragment thereof according to claim 1, which is the monoclonal antibody.

3. A composition for detecting human CD26, the composition comprising the anti-human CD26 monoclonal antibody or the antigen-binding fragment thereof according to claim 1.

4. The composition according to claim 3, wherein detection of human CD26 is detection by immunostaining.

5. The composition according to claim 4, wherein the detection of human CD26 is performed for a fixed tissue preparation.

6. The composition according to claim 5, wherein the fixed tissue preparation is obtained by fixation by treatment with formalin and/or paraffin embedding.

7. A method for detecting human CD26, the method comprising:
    contacting an anti-human CD26 monoclonal antibody or an antigen-binding fragment thereof according to claim 1 with a sample derived from a subject; and
    detecting human CD26, if present, in the sample by immunostaining.

8. The method according to claim 7, further comprising: determining the suitability of administration of an antibody for treatment of a human CD26-related disease according to the degree of detection of human CD26 in the immunostaining.

9. The method according to claim 7, wherein the human CD26-related disease is a cancer, an immune disease, a viral disease, or a metabolic disease.

10. The method according to claim 9, wherein the cancer, the immune disease, the viral disease, or the metabolic disease is selected from the group consisting of malignant mesothelioma, liver cancer, kidney cancer, prostate cancer, colorectal cancer, lung cancer, thyroid gland cancer, T-cell malignant lymphoma, gastrointestinal stromal tumor (GIST), glioma, autoimmune disease, graft versus host disease (GVHD), disease caused by coronavirus, and diabetes mellitus.

11. A process, comprising detecting human CD26 with the anti-human CD26 monoclonal antibody, or the antigen-binding fragment thereof, according to claim 1.

12. The anti-human CD26 monoclonal antibody or an antigen-binding fragment thereof according to claim 1, which is produced by a hybridoma deposited under Accession No. NITE BP-01642.

13. The anti-human CD26 monoclonal antibody or an antigen-binding fragment thereof according to claim 1, which is produced by a hybridoma deposited under Accession No. NITE BP-01643.

14. The anti-human CD26 monoclonal antibody or an antigen-binding fragment thereof according to claim 1, which is produced by a hybridoma deposited under Accession No. NITE BP-01644.

15. A hybridoma selected from the group consisting of a hybridoma deposited under Accession No. NITE BP-01642, a hybridoma deposited under Accession No. NITE BP-01643, and a hybridoma deposited under Accession No. NITE BP-01644.

16. The hybridoma according to claim 15, which is the hybridoma deposited under Accession No. NITE BP-01642.

17. The hybridoma according to claim 15, which is the hybridoma deposited under Accession No. NITE BP-01643.

18. The hybridoma according to claim 15, which is the hybridoma deposited under Accession No. NITE BP-01644.

* * * * *